(12) United States Patent
Lee

(10) Patent No.: US 9,439,829 B2
(45) Date of Patent: Sep. 13, 2016

(54) VIBRATION ANALGESIA INJECTION APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 646 days.

(21) Appl. No.: 13/892,288

(22) Filed: May 12, 2013

(65) Prior Publication Data

US 2014/0336548 A1    Nov. 13, 2014

(51) Int. Cl.
| | | |
|---|---|---|
| *A61B 17/20* | (2006.01) | |
| *A61H 23/02* | (2006.01) | |
| *A61M 5/42* | (2006.01) | |
| *A61B 17/32* | (2006.01) | |
| *A61C 1/14* | (2006.01) | |
| *A61M 39/16* | (2006.01) | |

(52) U.S. Cl.
CPC .......... *A61H 23/02* (2013.01); *A61H 23/0218* (2013.01); *A61H 23/0263* (2013.01); *A61M 5/422* (2013.01); *A61B 17/320068* (2013.01); *A61C 1/148* (2013.01); *A61M 2039/167* (2013.01)

(58) Field of Classification Search
CPC .......... A61M 5/422; A61M 2039/167; A61B 17/320068; A61C 1/148
USPC ............................................. 604/22; 601/46
See application file for complete search history.

(56) References Cited

U.S. PATENT DOCUMENTS

| | | | |
|---|---|---|---|
| 3,467,925 A * | 9/1969 | Masuda | H02K 33/18 310/27 |
| 3,620,209 A | 11/1971 | Kravitz | |
| 5,300,029 A * | 4/1994 | Denance | A61M 5/20 128/DIG. 1 |
| 6,231,531 B1 | 5/2001 | Lum | |
| 8,121,696 B2 | 2/2012 | Vallero | |
| 8,147,533 B2 | 4/2012 | Baxter | |
| 2007/0088385 A1 | 4/2007 | Perry | |
| 2008/0086063 A1 | 4/2008 | Baxter | |
| 2008/0086159 A1 | 4/2008 | Zweifler | |
| 2008/0255483 A1 | 10/2008 | Goldberg | |
| 2009/0004628 A1* | 1/2009 | Knutson | A61C 19/08 433/215 |
| 2011/0022115 A1 | 1/2011 | Salzhauer | |
| 2011/0054386 A1 | 3/2011 | Blaine | |
| 2011/0288456 A1 | 11/2011 | Vallero | |
| 2012/0179099 A1 | 7/2012 | Baxter | |

OTHER PUBLICATIONS

Giordano J: The neurobiology of nociceptive and antinociceptive systems. 2005; 8:277-290, Pain Physician. USA.

(Continued)

*Primary Examiner* — Matthew F Desanto

(57) ABSTRACT

The present invention presents a hypodermic injection apparatus and methods to introduce an agent to a human body in a less painful way by activating inhibitory mechanisms for pain perception. The apparatus comprises a vibration assembly that encircles a needle penetration site, a removable and disposable barrier device that isolates the apparatus from a recipient and from a needle, a mechanical assembly for syringe movement and a power and control electronics housed in a handle assembly. The vibration assembly generates and delivers vibration to the recipient through a resonant vibration chamber that contacts the recipient via the barrier device. A syringe needle penetrates the recipient's tissue through a linear tubular conduit axially located in the vibration chamber. The needle penetration site is encircled by vibration and the needle is enclosed by the barrier device while being retracted from the recipient.

16 Claims, 14 Drawing Sheets

(56) References Cited

OTHER PUBLICATIONS

Hudspith MJ, Siddall PJ, and Munglani R: Physiology of pain. 2006. Foundations of anesthesia, second edition. Elsevier Mosby, NY, USA.

Charlton JE: Stimulation-produced analgesia. 2005. Core Curriculum for Professional Education in Pain. IASP Press, Seattle, USA.

Smith KC, Comite SL, Balasubramanian S, Carver A, Liu JF; Vibration anesthesia: A noninvasive method of reducing discomfort prior to dermatologic procedures. Dermatology Online Journal 10 (2):1, USA.

Hollins M, Roy EA, Crane SA: Vibratory antinociception: Effects of vibration amplitude and frequency. Sep. 2003;4 (7):381-391. J Pain, Elsevier. NY, USA.

Zoppi M, Voegelin MR, Signorini M, Zamponi A: Pain threshold changes by skin vibratory stimulation in healthy subjects. Dec. 1991;143(4):439-443. Acta Physiol Scand, Wiley-Blackwell, NJ, USA.

Roy EA, Hollins M, Maixner W: Reduction of TMD pain by high-frequency vibration: a spatial and temporal analysis. Feb. 2003;101(3):267-274. Pain. Elsevier. NY, USA.

* cited by examiner

Figure 4
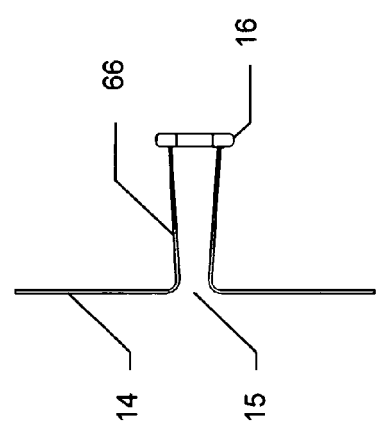
A
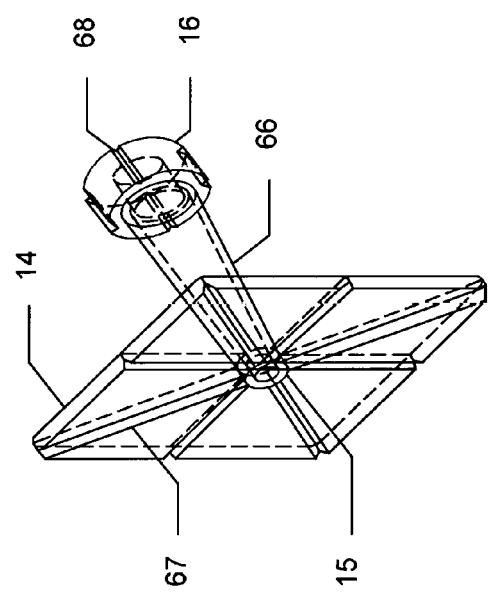
B

VIBRATION ANALGESIA INJECTION APPARATUS

CROSS REFERENCE TO RELATED APPLICATIONS

Attached please refer to the Information Disclosure Statement for the cross reference to related applications.

STATEMENT REGARDING FEDERALLY SPONSORED RESEARCH OR DEVELOPMENT

The present invention is not a federally sponsored research or development.

TECHNICAL FIELD

The present invention relates generally to the field of hypodermic injection of an agent for medical purpose. More specifically, the present invention provides an apparatus and methods to reduce pain and discomfort associated with an entry of both a needle and an injectable agent into tissue.

BACKGROUND OF THE INVENTION

Injection of an agent into cutaneous and muscle tissues through a needle prick disrupts mechanical and chemical stability of the tissue and initiates a series of electrophysiological and biochemical cascade in the local tissue environment and in free nerve endings of nociceptive primary afferent nerve fibers embedded in the tissue. Cationic channels of the free nerve endings are activated, dependent on biophysical properties of both the needle prick and injected agent. Once voltage gated Na+ channels are activated, membrane depolarization of the nociceptor is propagated, resulting in release of intracellular Ca++. The increase in Ca++ concentration mediates cellular and microenvironmental changes to sensitize nociceptors of the free nerve endings. Furthermore, cells that are disrupted by needle prick could release membrane fatty acids which convert to prostaglandins. Increase in prostaglandins could intensify nociceptive response of the free nerve endings, which translates into intensified painful sensation by a subject.

The majority of the nociceptive signals generated by the free nerve endings are transmitted via both A-delta and C nerve fibers to superficial dorsal horn of the spinal cord. A-delta nerve fibers are responsible for initial sensation of sharp localized pain and C fibers are responsible for so-called second pain of burning and bruised feeling over a wider area than perceived by the A-delta fibers. A-delta fibers are known to be sensitized by intense heat, and high intensity and prolonged activation of C fibers are known to perpetuate the sensitization cycle of C fibers by producing ligands acting on release of pro-inflammatory molecules. At the spinal cord, both A-delta and C-fibers produce glutamate that is a key molecule for transmission of sensation of pain. Postsynaptic nociceptive input then travels upward from the spinal cord to various parts of brain.

There are inhibitory neuronal signals arising from various parts of the brain that descend in the spinal cord to modulate nociception. Descending inhibitory signals may be activated by external factors including stimulation on peripheral or central nervous system. In addition, there are ascending inhibitory signals, albeit minor, arising from parts of the brain. Descending inhibitory signals come to various neuronal structures of the dorsal horn of the spinal cord where downward postsynaptic changes inhibit nociceptive responses. It is believed that in human subjects the descending inhibitory signals can be physically activated by acupuncture, transcutaneous electric nerve simulation (TENS), vibration, dorsal column stimulation and deep brain stimulation.

Vibration is one of peripheral stimulation methods to reduce nociception, which include TENS, acupuncture, acupuncture-like TENS, electroacupuncture and acupressure. Exact mechanisms of analgesia induced by vibration have not been clarified yet but it is believed to be related to activation of A-beta primary afferent nerve fibers that inhibit segmental neurons of the dorsal horn of the spinal cord. It is also proposed that vibration stimulates both high-threshold A-beta fibers and A-delta fibers, which activates the descending inhibitory signals to suppress the dorsal horn neurons. Clinically, both TENS and vibration have been shown to reduce acute and chronic pain conditions, including low back pain, acute orofacial pain, causalgia, pain associated with vaginal delivery of baby and arthritic pain. In particular, vibration of cutaneous tissue of patients has been shown to reduce pain associated with needle prick and injection of agents into the tissue, thereby reducing requirement of anesthetic agents for minor procedures on skin and its appendages.

Various frequencies have been studied for vibration induced analgesia, ranging from 20 Hz to 300 Hz with a varying degree of effectiveness on analgesia. Additional issues of vibration such as duration, amplitude and effective area and depth under vibration have not been studied for its comparative effectiveness except that it appears that analgesia is achieved best in an area directly under vibration. Shortcomings of vibration are short duration of effects and potential development of tolerance over repetitive uses.

Needle-free injection systems using high-pressure jet-stream have been developed over a few years to reduce discomfort of needle prick necessary for injecting agents into tissue. However, needle-free injection disrupts mechanical and chemical stability of the tissue, which initiates similar electrophysiological and biochemical responses in nociceptive primary afferent nerve fibers to needle-based injection systems. Diffuse but limited dispersion from a site of entry of pressured jet-stream of the needle-free system inside the tissue along a longitudinal injection path may be the only advantage of the needle-free system to the needle-based system that produces a radially globular expansion of an injected agent from a tip of a needle inserted in the tissue. It is conceivable that globular expansion of the injected agent, compared to the longitudinally diffuse dispersion of the agent, may exert a more outward pressure per an area of the tissue, thereby disrupting a larger amount of mechanical connection of the tissue. However, one major drawback of the needle-free injection system is a risk of contamination of injection nozzle by recipient's tissue fluid that may emanate from an entry site of injection of the recipient. Unless each device is used only once for each recipient, it poses a significant hazard of transmission of potentially infectious agents such as hepatitis virus or human immunodeficiency virus (HIV) to other recipients receiving injection using the same device. Disposable needle-free injection systems would be available yet their cost-effectiveness cannot be compared favorably to simple disposable syringes and steel needles.

Intensity of nociception, i.e., pain sensation, associated with conventional hypodermic injection of an agent may be ameliorated by limiting extent of mechanical and chemical disruption of a target tissue and by activating descending inhibitory signals. Thinner and shorter hypodermic needles with a more acute angle of bevel may reduce the extent of mechanical disruption of the tissue. Stimulation of an injection site by vibration is one of available methods to activate the descending inhibitory signals. Successful implementation of vibration for achieving analgesia during the needle-based injection would require generation of a vibration field surrounding both a needle penetration site and a tissue infiltration site of an injected agent for an adequate length of time, adequate and redundant activation of primary afferent nerve fibers and fast diffusion of the injected agent from the tip of a needle to adjacent tissues without forming an outwardly pressured globule of the agent in an isolated area of the tissue. Yet the foremost importance should be given to a reproducible method of fail-safe delivery of an agent to a recipient without a risk of contamination by biologic fluids.

SUMMARY OF THE INVENTION

To achieve on-site placement of vibration surrounding a needle penetration site and a tissue infiltration site of an injected agent, adequate activation of adjoining primary afferent nerve fibers of the descending inhibitory signals by vibration, vibration-facilitated diffusion of an injected agent in the tissue and elimination of a risk of contamination of the apparatus by biologic fluids, the current apparatus comprises a vibration assembly, a mechanical assembly for syringe movement and a removable and disposable barrier that isolates the apparatus from recipient. The mechanical assembly further comprises a syringe holder assembly, a syringe propulsion assembly and a trigger assembly which is attached to a handle assembly. The handle assembly houses a electronic controller and a power source. A hypodermic needle of a syringe penetrates a tissue through a linear tubular conduit of the vibration assembly that contacts a skin of a recipient and delivers an injectable agent to the tissue while a field of vibration encircling the needle penetration site is applied to said tissue by the vibration assembly.

In one embodiment, the current apparatus is provided as a plurality of operating devices having one or a plurality of mechanical configurations. One of the configurations has a rectangular tubular body that is connected on a lower side of said tubular body to an elliptically tubular handle assembly at an angle to a longitudinal axis of said rectangular tubular body. A proximal end of the rectangular tubular body is connected to a vibration assembly and an upper side of said body houses a syringe holder assembly. A syringe propulsion assembly is housed longitudinally inside said body and is mechanically connected to the syringe holder assembly to slidably move the syringe holder on the upper side of said body along the longitudinal axis. A trigger assembly is attached to a front of the handle assembly, which initiates forward movement of the syringe propulsion assembly and retracts a needle from a recipient following completion of an injection.

In one embodiment, the vibration assembly, provided as one or a plurality of operating devices having one or a plurality of mechanical configurations, comprises a vibration generator and a vibration chamber which is connected to the vibration generator. The vibration chamber, provided in one or a plurality of mechanical configurations including a closed box configuration, contacts a recipient's skin and transmits vibration produced by the vibration generator to said skin and an underlying tissue. An upper part of the vibration chamber has an axially linear tubular conduit that runs from a distal end to a proximal end of said chamber. An aperture of the linear tubular conduit opens to a center of a recipient contact portion at the proximal end of the vibration chamber and the opposite side of said tubular conduit opens to the distal end of said chamber. The linear tubular conduit provides a hypodermic needle with a tubular passageway inside the vibration chamber to penetrate a tissue of a recipient.

In one embodiment, vibration is generated by an electromagnetic voice coil actuator with a moving coil, provided in one or a plurality of configurations, releasably and axially inserted in one or a plurality of cylindrical permanent magnets of said voice coil actuator. In a second embodiment, vibration is generated by an electromagnetic solenoid coil, provided in one or a plurality of configurations, releasably and axially inserted in one or a plurality of cylindrical permanent magnets. In another embodiment, vibration is produced by a vibratory electromagnetic motor provided as one or a plurality of mechanical configurations including an eccentric mass rotary motor or by an electromagnetic disc vibrator. A proximal end of the moving coil of the voice coil actuator, the vibratory rotary motor, or the disc vibrator is irreversibly attached to a vibration panel provided in one or a plurality of mechanical configurations including a diaphragmatic cone configuration. The vibration panel is attached to a part of the distal end of the vibration chamber and transmits vibration to the vibration chamber.

In one embodiment, a vibration chamber provides a resonant space in one or a plurality of mechanical configurations, which amplifies vibration in a certain range of frequencies generated by a vibration generator. A proximal end of the resonant space is configured to contact skin and to deliver resonated vibration. A distal end of the resonant space is configured to be attached to the vibration panel that transmits vibration to said resonant space. One of the mechanical configurations of the resonant space provides a natural frequency of said resonant space matched to a frequency range from 20 Hz to 300 Hz. The vibration chamber may or may not have a closed resonant space inside said chamber. A vibration chamber without a resonant space is configured as flat panel to which the vibration panel is directly attached.

In one embodiment, a moving coil of a voice coil actuator produces electromagnetic vibration in one or a plurality of frequencies ranging from 20 Hz to 20 kHz and of one or a plurality of amplitudes. In another embodiment, the voice coil actuator simultaneously generates vibration of multiple frequencies. Concurrent generation of multiple frequencies of vibration is meant to cover a wide range of nociceptive primary afferent nerve fibers which may have individually distinctive activation thresholds to different frequencies for activating inhibitory signals. Vibration amplitude is provided as adjustable to penetration depth of needle into tissue and to volume of injectable agent. A deeper penetration of a needle into a tissue and a larger volume of an injectable agent require a wider and deeper vibration field to sufficiently encompass the area of the injection, compared to a shallow penetration and to a smaller injection volume. Force of vibration is proportional to amplitude of vibration, which suggests that a higher amplitude is required to generate a larger force of vibration to cover a larger three-dimensional volume of a tissue that needs to be vibrated. Electromagnetic disc vibrator is also provided in one or a plurality of frequencies and with one or a plurality of amplitudes. The disc vibrator also is configured to simultaneously generate vibration of multiple frequencies. Vibratory eccentric mass rotary motor is provided in frequency that is variable.

In one embodiment, a control unit and a power source for the vibration assembly are housed in a handle assembly and connected electrically to the vibration generator. The control unit, provided as one or a plurality of electronic configurations, supplies the vibration generator an alternating or direct current and modulates both frequency and amplitude of vibration. The power source includes alternating current that is carried to the current apparatus from an external electric source or direct current from one or a plurality of batteries.

In one embodiment, a removable and disposable barrier, provided in one or a plurality of configurations, is insertably placed in the linear tubular conduit located in the vibration chamber along the longitudinal axis. One of the configurations includes a thin sheet of round or rectangular shape covering a recipient contact portion of the vibration chamber, which merges with a barrier tube inside the linear tubular conduit of the vibration chamber and gets connected to a round ring of said barrier located outside a distal end of said linear tubular conduit. The ring portion of the barrier protrudes distally from the distal end of the vibration chamber. The sheet is configured as thin membrane preferably made of a polymer and is indented on a recipient contact side. Indentations, provided as one or a plurality of configurations including linear indentation in a radial direction from a center of said sheet, are to facilitate folding of the sheet into a tubular configuration when the barrier is withdrawn through the linear tubular conduit from the proximal end to the distal end of the vibration chamber.

In one embodiment, a needle of a syringe coaxially enters a barrier tube releasably inserted in the linear tubular conduit of the vibration chamber through the ring portion of the barrier located at the distal end of said vibration chamber and protrudes from an open center of the sheet of the barrier located at the proximal end of said vibration chamber to penetrate a tissue of a recipient. Upon a full advancement of the needle for tissue penetration, the ring portion of the barrier circumferentially and adherently grabs a hub of the needle. Following completion of an injection, the needle coaxially retracts back out together with the adherent ring portion of the barrier from the linear tubular conduit of the vibration chamber. On retraction inside the linear tubular conduit of the vibration chamber, the sheet of the barrier is folded to form a longitudinally corrugated tubular sheet encircling the needle. Both the needle of the syringe and barrier are then discarded as a single unit. The barrier shields the vibration chamber with the linear tubular conduit from the needle during an entire cycle of penetration into and withdrawal of the needle from the recipient, thereby preventing contamination of the apparatus by biologic fluids of the recipient.

In one embodiment, a syringe attached to a needle is placed in a syringe holder assembly that is connected to a syringe propulsion assembly in one or a plurality of mechanical configurations. The syringe holder assembly, provided as one or a plurality of operating devices with one or a plurality of mechanical configurations, releasably encloses and slidably moves both the syringe and needle along the longitudinal axis of the apparatus on a top of the syringe propulsion assembly. In one mechanical configuration, the syringe holder assembly comprises a syringe holder and a syringe holder rail assembly. A syringe propulsion assembly comprises a syringe holder positioning assembly, a syringe holder thrust assembly and a plunger thrust assembly. The syringe holder rail assembly which is attached to a bottom of the syringe holder slides on the top of the syringe propulsion assembly to move back and forth a syringe and a needle. The syringe holder positioning assembly which is located at a distal end of the syringe holder reversibly advances said syringe holder longitudinally to secure the needle of the syringe inside the linear tubular conduit of the vibration chamber. Both the syringe holder thrust and plunger thrust assemblies, provided as one or a plurality of operating devices having one or a plurality of mechanical configurations, push the syringe holder and the plunger forward, respectively, by releasing compressed compression springs located at a distal end of each thrust.

In one embodiment, longitudinal sliding movement of the syringe holder is accomplished by a two-stage propulsion by the syringe propulsion assembly. The first stage is to position the needle of the syringe inside the linear tubular conduit of the vibration chamber by forwardly advancing the syringe holder positioning device. The second stage is to thrust both the syringe holder assembly and a plunger of the syringe toward the vibration chamber. Both the syringe holder assembly and the plunger of the syringe may be thrust either simultaneously or sequentially. Short syringes with small volume injectable may be thrust by a single propulsion mechanism using one or a plurality of compression springs axially placed behind a plunger of a syringe housed in the syringe holder. It may be advantageous for long syringes with large volume injectable to have separate propulsion mechanisms, with one mechanism for needle penetration to a tissue and the other for pushing a plunger to inject an agent into the tissue.

In one embodiment, propulsion of the syringe holder assembly is initiated by a mechanical trigger assembly with a trigger lever and a trigger bar, which is provided as one or a plurality of mechanical configurations. The trigger lever is attached to the handle assembly via a hinge joint and can be squeezed manually toward the handle assembly in pivoting movement about the joint. On an inner wall of the trigger lever, there is provided the trigger bar in one or a plurality of configurations, which is irreversibly attached to the inner wall of the trigger lever at an angle. Once the trigger lever is squeezed close to the handle assembly, the trigger bar comes in contact with a pawl lever of the syringe holder thrust and releases a ratchet of the syringe holder thrust from the pawl. The syringe holder thrust then is pushed forward by expansion of the compression spring located axially behind the syringe holder thrust. The plunger is pushed forward by similar expansion of the compression spring of the plunger thrust that is anchored by a separate pawl. A lever of the plunger thrust pawl is movably located behind the pawl lever of the syringe holder thrust and can be reversibly lifted by an incoming trigger bar to release a plunger thrust ratchet.

In one embodiment, the trigger assembly is configured to retract the syringe holder assembly for a distance following completion of an injection to pull out the needle from the recipient. On both sides of the trigger bar, there is provided a pair of connecting rods which connect the trigger lever to the syringe holder thrust. Each rod is rotatably connected to a hinge joint of the trigger lever and to another hinge joint of the syringe holder thrust. Both rods are horizontally connected to each other by a pair of horizontal bars. A horizontal bar of the rods at the trigger is located below the hinge joint of the trigger. The other horizontal bar of the rods at the syringe holder thrust is located above the hinge joint of the syringe holder thrust. Asymmetric placement of the horizontal bars above and below the hinge joints along the longitudinal axis of the connecting rods allows unobstructed movement of the trigger lever to the handle assembly. Upon a release of the trigger lever, the trigger connecting rods push back the syringe holder thrust for a distance by downward pressure on the hinge joint of the syringe holder thrust generated by the horizontal bar at said hinge joint.

BRIEF DESCRIPTION OF THE DRAWINGS

FIG. 2A represents a profile view; FIG. 2B shows a top-down view; FIG. 2C shows a frontal view.

FIG. 3A represent an example of a vibration chamber attached to an electromagnetic vibration generator; FIG. 3B shows an example of an electromagnetic disc vibrator; FIG. 3C shows an eccentric mass vibratory motor.

FIG. 4 shows a schematic example of a removable and disposable barrier device; FIG. 4A represents a cross-sectional lateral view; FIG. 4B shows a three-dimensional view.

FIG. 5A shows a fully assembled upper part of the syringe holder assembly; FIG. 5B shows an example of a syringe holder thrust assembly; FIG. 5C shows an open view of the upper part of the syringe holder.

FIG. 6A shows a upside-down bottom view of syringe holder rails with rail-lock knobs; FIG. 6B shows an exposed view of the syringe holder rail locks located on a top of the syringe holder thrust.

FIG. 7A depicts individual components of the plunger thrust; FIG. 7B shows a view of an inner tubular space of the plunger thrust where a compression spring is inserted in; FIG. 7C shows an assembled view of the plunger thrust with the open syringe holder.

FIG. 8A shows a schematic illustration of a method of engagement of the plunger thrust with the plunger thrust housing; FIG. 8B shows a schematic view of the plunger thrust housing assembled with the apparatus.

FIG. 10A represents a schematic view of the syringe holder positioner; FIG. 10B shows mechanisms of locking and unlocking the syringe holder positioner; FIG. 10C shows a schematic example of a syringe holder positioner housing adjoining a distal end of the syringe propulsion assembly compartment.

FIG. 11A depicts a syringe holder thrust; FIG. 11B shows a trigger lever and a trigger bar; FIG. 11C shows a pair of trigger connecting rods assembled with a pair of horizontal bars; FIG. 11D shows a profile view of the trigger connecting rod and the horizontal bars.

FIG. 12A shows individual components of the needle depth control device; FIG. 12B shows an assembled view of the needle depth control device.

DETAILED DESCRIPTION OF THE DRAWINGS

As described below, the present invention provides a vibration analgesia injection apparatus and methods of use. It is to be understood that the descriptions are solely for the purposes of illustrating the present invention, and should not be understood in any way as restrictive or limited. Embodiments of the present invention are preferably depicted with reference to FIGS. 1 to 13, however, such reference is not intended to limit the present invention in any manner. The drawings do not represent actual dimension of devices, but illustrate the principles of the present invention.

Figure 1:
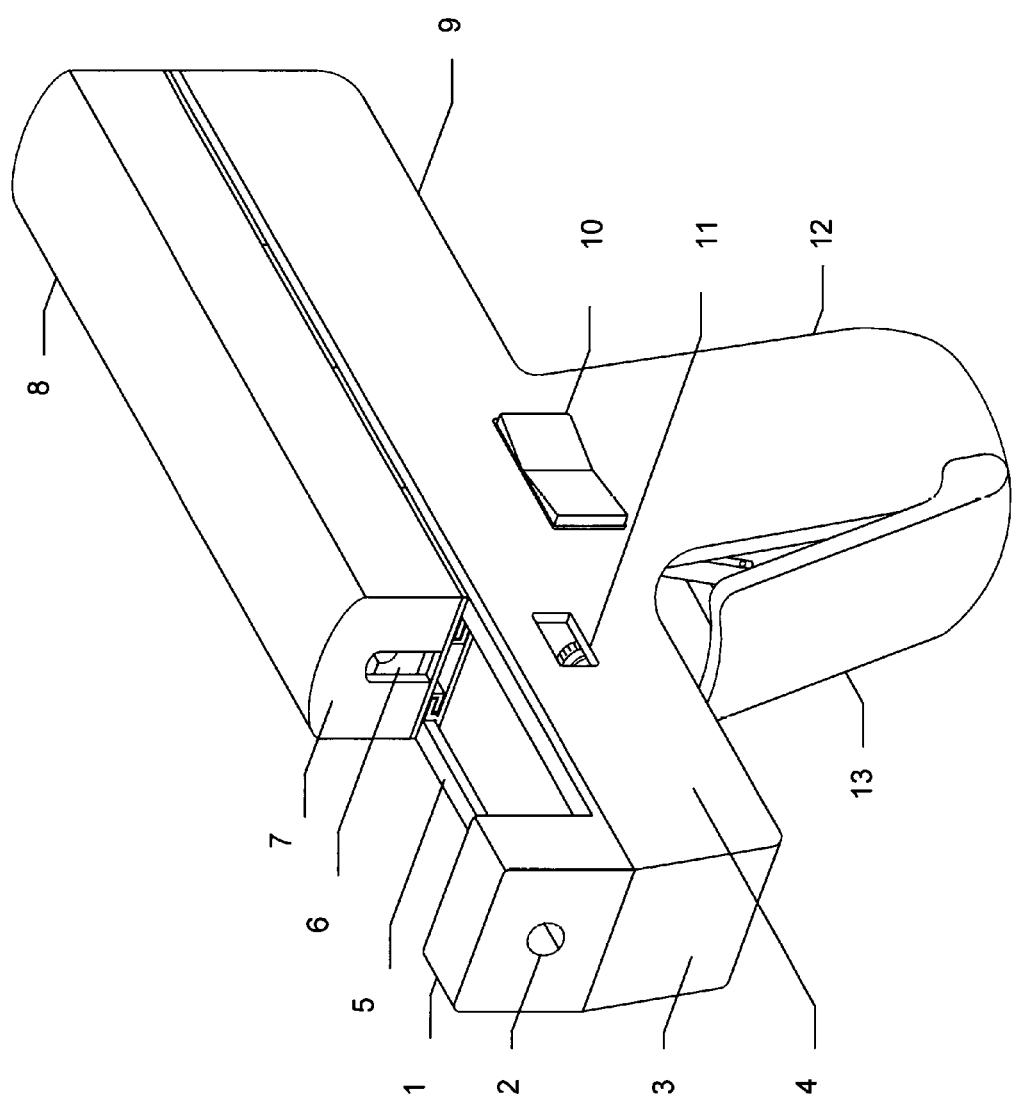
FIG. 1 shows an example of itemized components of the apparatus in a schematic three-dimensional view.

FIG. 1 shows an itemized view of the schematic example of individual devices of the apparatus. A vibration assembly comprises an upper vibration chamber 1, an open aperture 2 of a linear tubular conduit axially placed in the upper vibration chamber 1, a lower vibration chamber 3 and a housing 4 of a vibration generator. A syringe holder 8 which is a part of a syringe holder assembly movably sits atop a pair of rails 5 of a syringe propulsion assembly compartment 9. A front 7 of the syringe holder 8 shows an opening 6 of the syringe holder through which a needle of a syringe protrudes. An electronic controller switch 10 is positioned at a junction between a handle assembly 12 and a syringe propulsion assembly compartment 9. An open window 11 for needle depth control is located on a proximal side of the syringe propulsion apparatus compartment. The handle assembly 12 is attached to a bottom of the syringe propulsion assembly compartment 9 at an angle. A trigger assembly 13 is attached to the handle assembly at a hinge joint on each side of said handle assembly.

Once the apparatus is turned on by the electronic controller switch 10, vibration are generated by the vibration generator inside the housing 4. The vibration is transmitted to the vibration chamber 1 and 3 where vibration of one or a plurality of frequencies is resonated. The vibration then is delivered to a tissue of a recipient through a proximal end of the upper vibration chamber 1. A syringe with a needle is housed inside the syringe holder 8, with its needle protruding through the front opening 6 of the syringe holder 8. Once the trigger assembly 13 is fully squeezed toward the handle assembly 12, the syringe holder 8 slidably is thrust to the upper vibration chamber 1 of the apparatus by a syringe propulsion assembly housed in the syringe propulsion assembly compartment 9. The needle of the syringe penetrates the tissue through the open aperture 2 of the linear tubular conduit in the upper vibration chamber 1. Following completion of an injection, the syringe with its needle is linearly withdrawn by a returning trigger assembly 13 back to an original position of said trigger assembly.

Figure 2:
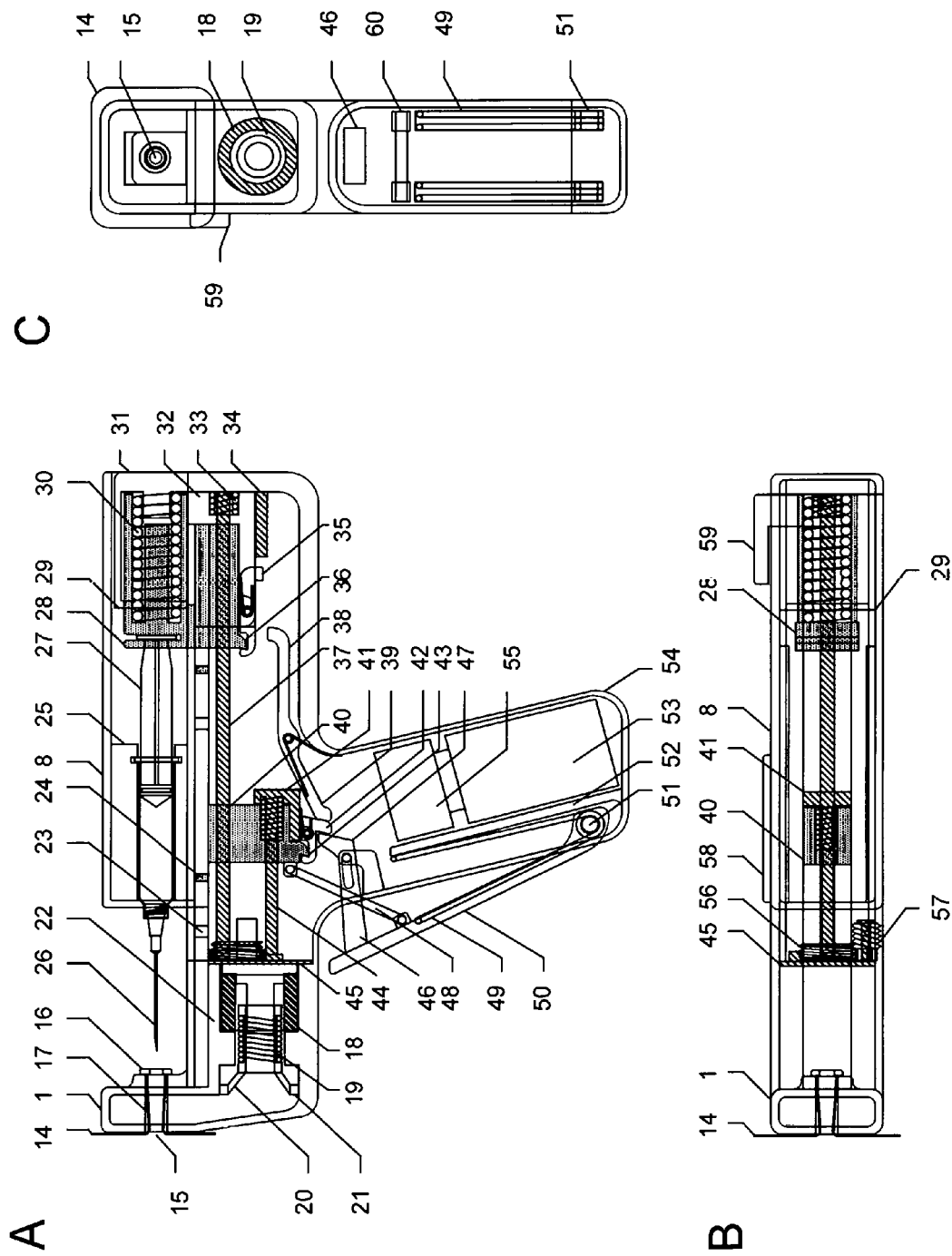
FIG. 2 shows a schematic two-dimensional example of individual components of the apparatus.

FIG. 2 shows schematic profile views of individual components of the apparatus. FIG. 2A shows a lateral view, FIG. 2B shows a top-down view and FIG. 2C shows a frontal view. A removable and disposable barrier device shows a barrier sheet 14, a tubular barrier center 15 and a barrier ring 16. The barrier is removably inserted in the linear tubular conduit 17 located in the center of the upper vibration chamber 1 in a direction from the proximal end to the distal end of the upper vibration chamber 1. The vibration generator, provided as one or a plurality of operating devices having one or a plurality of mechanical and electronic configurations, comprises a cylindrical permanent magnet 18 enclosed by a vibration generator housing cylinder 22, a moving coil 19 of a voice coil actuator that is irreversibly attached to a vibration diaphragm 20 in a cone configuration and a diaphragm attachment ring 21 to a vibration panel of the vibration chamber.

The handle assembly, provided as one or a plurality of operating devices having one or a plurality of mechanical configurations, comprises a pair of hinge joints 51 located at a proximal end of a bottom of the handle assembly on both sides, an inner handle divider 52, a battery pack 53, an outer wall of the handle 54 and a control electronics 55. The hinge joints 51 are rotatably connected with a trigger lever 50 of the trigger assembly. A trigger torsion spring 49 is inserted in a pivoting pin of each hinge joint 51 and exerts a circumferentially outward pressure on an inner wall of the trigger lever 50 and the inner handle divider 52. The battery pack 53 and the control electronics 55 are electrically connected to each other and to the voice coil actuator 19, and provide the voice coil actuator with electricity and electronic control on vibration for mode of vibration, frequencies and amplitudes. The batter pack 53 may be charged by wireless induction. A proximal end of the outer wall 54 of the handle is perforated to accommodate a trigger bar 46, a pair of trigger connecting rods 48 and a pair of the trigger torsion springs 49.

Shown in FIG. 2, a syringe cradle 25 of the syringe holder 8 houses a syringe which is connected to a needle 26 at a connecting tip of the syringe that protrudes from the syringe holder 8. A syringe plunger 27 is releasably and securely held by a plunger thrust 28. An upper part of a plunger thrust assembly located in the syringe holder 8, provided as one or a plurality of operating devices having one or a plurality of mechanical configurations, comprises the plunger thrust 28, a plunger thrust housing 29 which is provided in tubular configurations having an open proximal end and a closed distal end 31. A plunger thrust compression spring 30 is placed in a tubular space provided inside the plunger thrust 28. A lower part of the plunger thrust assembly located below a bottom of the syringe holder is anchored by a plunger thrust ratchet 36 and a plunger thrust pawl 35. The plunger thrust ratchet 36, provided in one or a plurality of configurations including a toothed projection, protrudes from a lower border of a proximal end of the lower part of the plunger thrust 28. The plunger thrust pawl 35, provided in one or a plurality of configurations, is attached to a syringe holder positioner assembly located distally behind a distal end of the lower part of the plunger thrust. The syringe holder positioner assembly comprises a syringe holder positioner 32, a positioner compression spring 33, a positioner supporter 34 and a positioner knob 59 that is connected to the syringe holder positioner 32. The positioner knob 59 outwardly protrudes from the syringe propulsion assembly compartment through a side wall of said compartment and is slidably movable and reversibly lockable. Once the positioner knob 59 is unlocked, said positioner knob slidably moves the syringe holder positioner 32 forward along a longitudinal axis of a plunger thrust guide shaft 37, driven by expansion of the compression spring 33. The syringe holder positioner 32 moves the syringe holder 8 forward until a plurality of rail lock knobs 24 of the syringe holder 8 are locked by corresponding rail locks 23 of a top plate of a syringe holder thrust assembly. Once the rail lock knobs 24 are locked by the rail locks 23 and the positioner knob 59 is locked, the needle 26 of the syringe is insertably placed in the linear tubular conduit 17.

The syringe propulsion assembly, provided as one or a plurality of operating devices having one or a plurality of mechanical configurations, comprises the plunger thrust assembly 28~31 and 36, the syringe holder positioner assembly 32~35 and the syringe holder thrust assembly in this particular schematic example. The syringe holder thrust assembly, provided as one or a plurality of operating devices having one or a plurality of mechanical configurations, comprises a syringe holder thrust 40, a syringe holder thrust guide shaft assembly 41 with a syringe holder thrust guide shaft 44, a syringe holder thrust ratchet 43 and a syringe holder thrust pawl 42. The syringe holder thrust ratchet 43, provided in one or a plurality of configurations including a toothed projection, protrudes from a bottom at a proximal end of the syringe holder thrust 40. The syringe holder thrust pawl 42, provided in one or a plurality of configurations, is attached to the syringe holder thrust guide shaft assembly 41. A compression spring is placed inside the syringe holder thrust 40 circumferentially wound around the syringe holder guide shaft 44 in front of the syringe holder guide shaft assembly 41 and provides forward movement of the syringe holder toward a proximal panel 45 of the syringe propulsion assembly compartment.

Forward movements of both the syringe holder thrust 40 and plunger thrust 28 are initiated by releasing both the ratchets 43 and 36 from the pawls 42 and 35, respectively. Release of both the ratchets 43 and 36 is accomplished by the trigger assembly. The trigger assembly, provided as one or a plurality of operating devices having one or a plurality of mechanical configurations, comprises the trigger lever 50, the trigger bar 46 with its trigger bar tip 47, a pair of the trigger connecting rods 48, a pair of horizontal bars (shown in FIG. 11) connected to the trigger connecting rods, a pair of the trigger torsion springs 49 and a plunger pawl release lever 38~39. The trigger bar 46 immovably attached to the inner wall of the trigger lever 50 reversibly projects the trigger bar tip 47 to a distal end of the syringe holder thrust pawl 42. The distal end of the syringe holder thrust pawl 42 is positioned anteriorly to a proximal knob 39 of the plunger pawl release lever. The plunger thrust pawl release lever 38~39 has a pivoting center located at a right angle to the longitudinal axis of the apparatus. A torsion spring is inserted in a pivoting pin of said pivoting center, providing circumferentially upward movement of the proximal knob of the plunger thrust pawl release lever.

In one embodiment, a forward positioning of the syringe holder 8 by a forward movement of the syringe holder positioner 32 vertically aligns a distal knob of the plunger thrust pawl 35 with a distal knob of the plunger thrust pawl release lever 38. The trigger lever 50 then is manually squeezed by an operator toward the outer wall 54 of the handle assembly. The trigger bar 46 advances distally toward a distal end of the apparatus and the trigger bar tip 47 pushes back the distal end of the syringe holder thrust pawl 42, thereby releasing the ratchet 43. At the same time, the distal end of the syringe holder thrust pawl 42 pushes down the proximal knob 39 of the plunger pawl release lever. Circumferentially downward movement of the plunger pawl release lever rotates the distal knob 38 of said plunger pawl release lever in a counterclockwise direction about the pivoting center of said plunger pawl release lever. The counterclockwise rotation of said distal knob 38 pushes up the distal knob of the plunger thrust pawl 35. Circumferentially upward movement of the distal knob of the plunger thrust pawl 35 about its pivoting center releases the ratchet 36. Release of both the ratchets 43 and 36 allows forward movement of both the syringe holder thrust and plunger thrust.

Depending on a distance between the distal end of the syringe holder thrust pawl 42 and the proximal knob 39 of the plunger pawl release lever, forward movement of both the syringe holder thrust and plunger thrust can be timed simultaneously or sequentially. The forward movement of the syringe holder thrust 40 makes the needle 26 penetrate a tissue of a recipient. The forward movement of the plunger thrust 28 pushes the plunger 27 toward the tip of the syringe, thereby delivering an injectable agent to the tissue. In one embodiment, the present apparatus may have the plunger thrust assembly and the syringe holder positioner assembly without the syringe holder thrust assembly. In another embodiment, the apparatus comprises the syringe holder thrust assembly, the plunger thrust assembly and the syringe holder positioner assembly, provided with both the distal end of the syringe holder thrust pawl 42 and the proximal knob 39 of the plunger pawl release lever separated by one or a plurality of distances from each other. Short syringes with a small volume injectable may be thrust by a single propulsion mechanism with the plunger thrust assembly. It may be advantageous for long syringes with a large volume injectable to have both the syringe holder thrust assembly and plunger thrust assembly, with one mechanism for needle penetration to a tissue and the other for pushing a plunger to inject an agent into the tissue.

The apparatus controls depth of needle in a tissue, provided by one or a plurality of operating devices having one or a plurality of mechanical configurations. In one embodiment, on a distal surface of the proximal panel 45 of the syringe propulsion assembly compartment, a needle depth control thread 56 is axially installed with a spiral needle depth control knob 57. The spiral needle depth control knob 57 is accessible from outside the syringe propulsion assembly compartment and is spirally joined in parallel with the spiral needle depth control thread 56. Rotation of the spiral needle depth control knob 57 rotationally moves the needle depth control thread 56 away from or toward the proximal panel 45, dependent on handedness of the spirals. Distance between the distal surface of the proximal panel 45 and a proximal end of the syringe thrust 40 is adjustable by moving the needle depth control thread 56 away from or toward the proximal panel 45.

The syringe holder 8 can be lifted open by a longitudinal syringe holder knob 58 located on a bottom on one side of said syringe holder 8.

Figure 3:
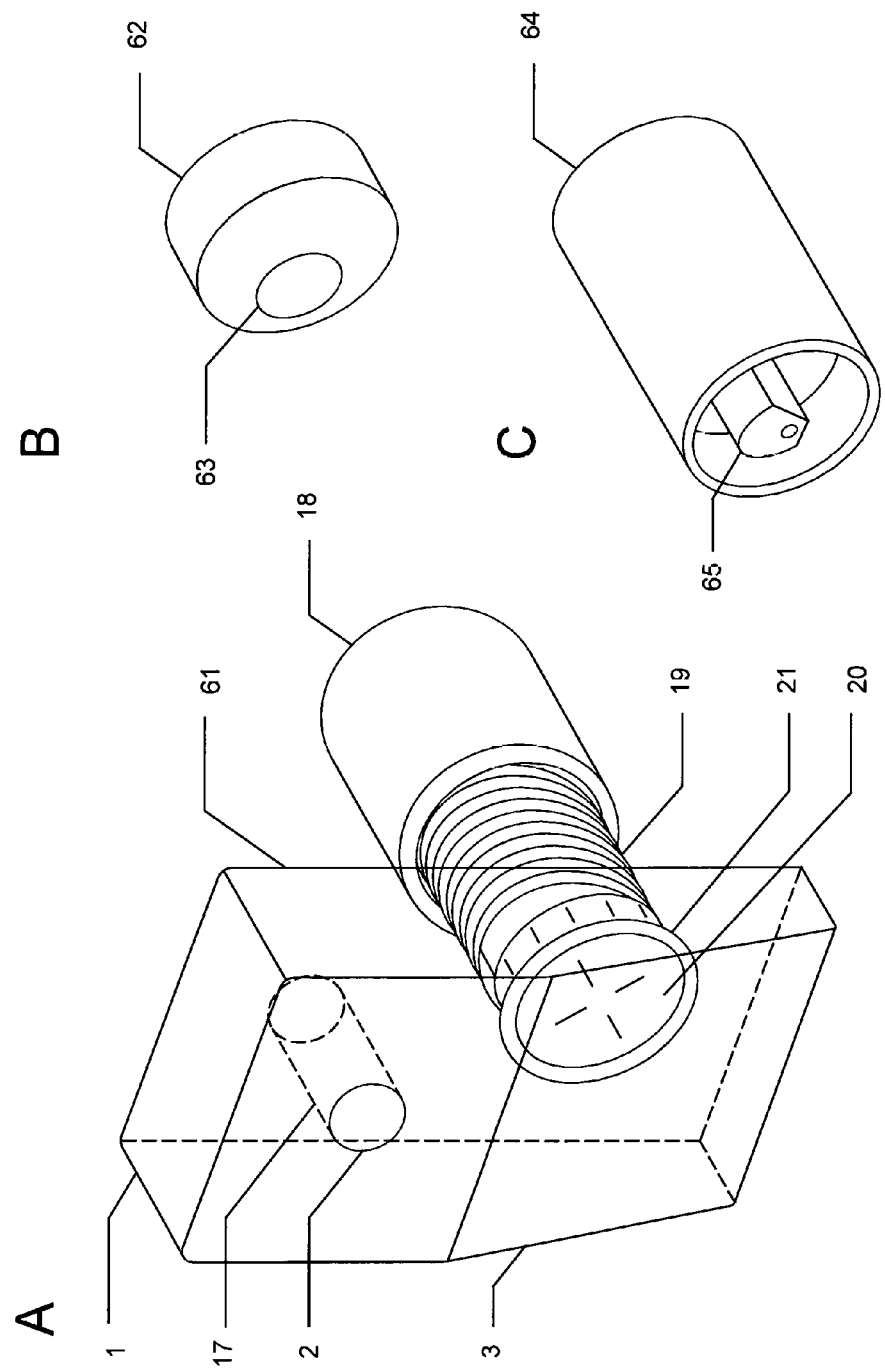
FIG. 3 shows a schematic example of a vibration assembly.

FIG. 3 shows a schematic illustration of an example of the vibration assembly and examples of vibration generators. FIG. 3A shows the vibration chamber comprising the upper vibration chamber 1 and the lower vibration chamber 3, a posterior wall of the vibration chamber 61, the cylindrical permanent magnet 18, the voice coil actuator 19, the vibration diaphragm 20 and the diaphragm attachment ring 21 attached to a vibration panel of the posterior wall 61. The linear tubular conduit 17 axially runs through the center of the upper vibration chamber 1 along the longitudinal axis and opens to the aperture 2. Referring to FIG. 2A, the voice coil actuator 19 is releasably inserted in the cylindrical permanent magnet 18 and receives electricity from the control and power source of the handle assembly. The cylindrical permanent magnet 18 is immovably fixed to the surrounding vibration generator housing cylinder and the voice coil actuator 19 axially moves back and forth inside said magnet 18 along the longitudinal axis dependent on electromagnetic polarity provided by the controller of the handle assembly. The axial movements of the voice coil actuator 19 generates vibration of the vibration diaphragm 20 which transmits vibration through the vibration panel to the vibration chamber. The vibration chamber resonates vibration in one or a plurality of frequencies and amplifies a range of frequencies. The proximal end of the upper vibration chamber 1 contacts a recipient's skin and delivers the vibration. A needle of a syringe slidably passes through the aperture 2 of the linear tubular conduit 17 and penetrates the tissue of the recipient. FIG. 3B depicts an electromagnetic disc vibrator 62 with its vibration portal 63. FIG. 3C shows a schematic example of an eccentric mass rotary vibration motor 64 with its eccentric mass 65 axially inserted along the longitudinal axis.

FIG. 4 shows a schematic example of a removable and disposable barrier device. FIG. 4A shows a profile view and figure B shows a three dimensional view. In this particular example, the barrier sheet 14 is configured as rectangular and merges with a longitudinal barrier tube 66 at the barrier center 15. The barrier tube 66 merges with the barrier ring 16. The barrier sheet 14 is configured as thin membrane and is linearly indented on a recipient contact side radiating from the barrier center 15 to an outer margin of said barrier sheet 14. The barrier ring 16 is made of an elastic polymer and has a plurality of axial indentations 68. The ring indentations 68 allow said ring to be circumferentially squeezed to become smaller with a shorter diameter. Referring to FIG. 3A, the squeezed ring 16 facilitates passing of said ring through the linear tubular conduit 17 in a direction from the proximal end to the distal end of the upper vibration chamber 1. Once protruding from the distal end of the linear tubular conduit 17, said ring expands and anchors against the posterior wall 61. An inner wall of the ring 16 is configured as adherent to a hub of the needle. One example of the inner wall adherence uses a biocompatible glue on a surface of said inner wall. Following completion of an injection, the barrier with its said ring 16 securely adherent to the hub of the needle is withdrawn by the retracting needle through the linear tubular conduit 17 from the proximal end to the distal end of the vibration chamber. The linear indentations 67 facilitate inward folding of the barrier sheet 14 to form a corrugated tubular configuration to encase a needle during the withdrawal of both the barrier and needle.

Figure 5:
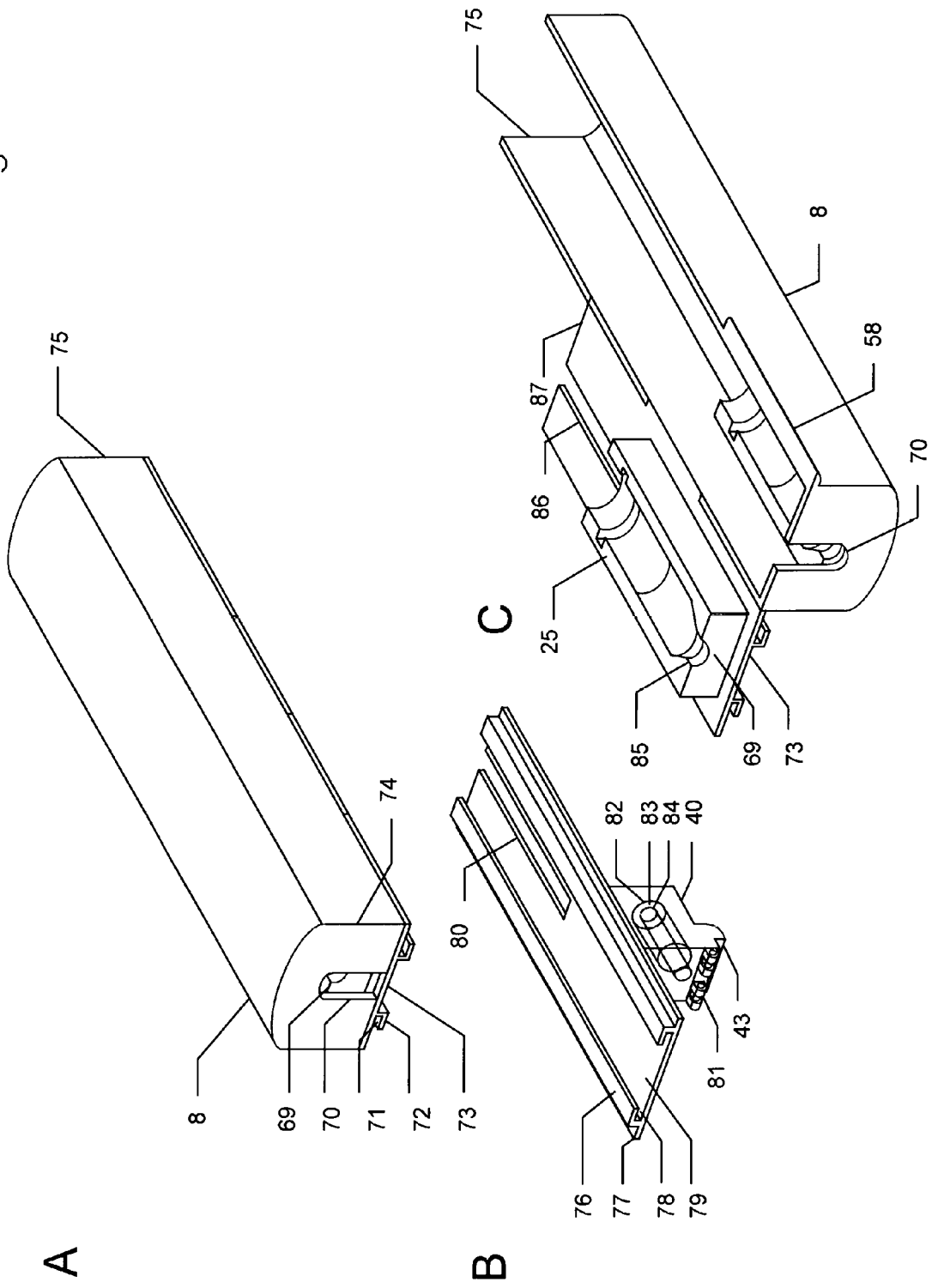
FIG. 5 shows a schematic example of a syringe holder assembly and a syringe holder thrust assembly.

FIG. 5 shows a schematic example of a syringe holder assembly. FIG. 5A shows a fully assembled upper part of the syringe holder assembly. The syringe holder 8 which runs longitudinally from a proximal end 74 to a distal end 75 sits atop a syringe holder bottom plate 73. Referring to FIG. 1, a central portion 70 of the proximal end 74 is cut out from a middle of said proximal end toward the syringe holder bottom plate 73, to form the proximal opening through which a syringe hub protrudes toward the upper vibration chamber 1. Referring to FIG. 2A, a proximal end 69 of the syringe cradle 25 is visualized through the cut-out portion 70 of the proximal end 74 of the syringe holder 8. The syringe holder bottom plate 73 has a pair of longitudinal rails 72 underneath said bottom plate close to each longitudinal lateral edge of said bottom plate. The longitudinal rails 72 form a pair of syringe holder rail slots 71, with each said slot corresponding to said rail 72.

FIG. 5B shows an example of a syringe holder thrust assembly. A pair of syringe holder thrust rails 76 are longitudinally located on a syringe holder thrust top plate 79 close to each longitudinal lateral edge of said top plate, which form a pair of syringe holder thrust rail slots 78, with each said slot corresponding to said rail 76. Each said thrust rail 76 of the top plate 79 slidably is inserted along the longitudinal axis in the corresponding slot 71 of the bottom plate 73. Likewise each said holder rail 72 of the bottom plate 73 is inserted in the corresponding slot 78 of the top plate 79. Referring to FIG. 1, a pair of lateral edges 77 of the top plate 79 are slidably inserted along the longitudinal axis in corresponding slots inside the rail 5 of the syringe propulsion assembly compartment 9. The top plate 79 has a slot 80 for a syringe holder thrust plunger which is rectangularly cut-out along the longitudinal axis in a central part of said top plate. The syringe holder thrust 40 is fixedly attached to a portion of an undersurface of the top plate 79 along the longitudinal axis. Referring to FIG. 2A, the bottom proximal edge of the syringe holder thrust 40 provides a hinge joint 81 for the trigger connecting rods 48 and the thrust ratchet 43 which is releasably anchored by the pawl 42. In a central portion of the syringe holder thrust 40, there is provided a cylindrically tubular space 83 for a compression spring which is to push said thrust 40 forward once said ratchet 43 is released from said pawl 42. The cylindrically tubular space 83 is formed by an outer tubular wall 82. Referring to FIG. 2A, a central tubular conduit 84 of said tubular space 83 is penetrated by the cylindrical syringe holder guide shaft 44 which guides linear movement of said syringe holder thrust 40.

FIG. 5C shows an open view of the upper part of the syringe holder. The syringe cradle 25 is configured to an outline of a syringe and provides a syringe hub portion 85 where a proximal end of a syringe rests. Corresponding to the syringe holder thrust plunger slot 80 of the top plate, the bottom plate 73 has a slot 86 for said thrust plunger which is rectangularly cut-out along the longitudinal axis in a central part of said bottom plate. A longitudinal length of the bottom plate 73 which is shorter than a length of the syringe holder 8 ends at a distal end 87. The syringe holder 8 has a longitudinal syringe holder knob 58 located on a bottom on one side of said syringe holder 8. Said longitudinal knob serves to open and close the syringe holder 8. Referring to FIG. 2A, the distal end 75 of the syringe holder 8 does not have a closing wall, which is to slide said holder 8 over the plunger thrust housing 29.

Figure 6:
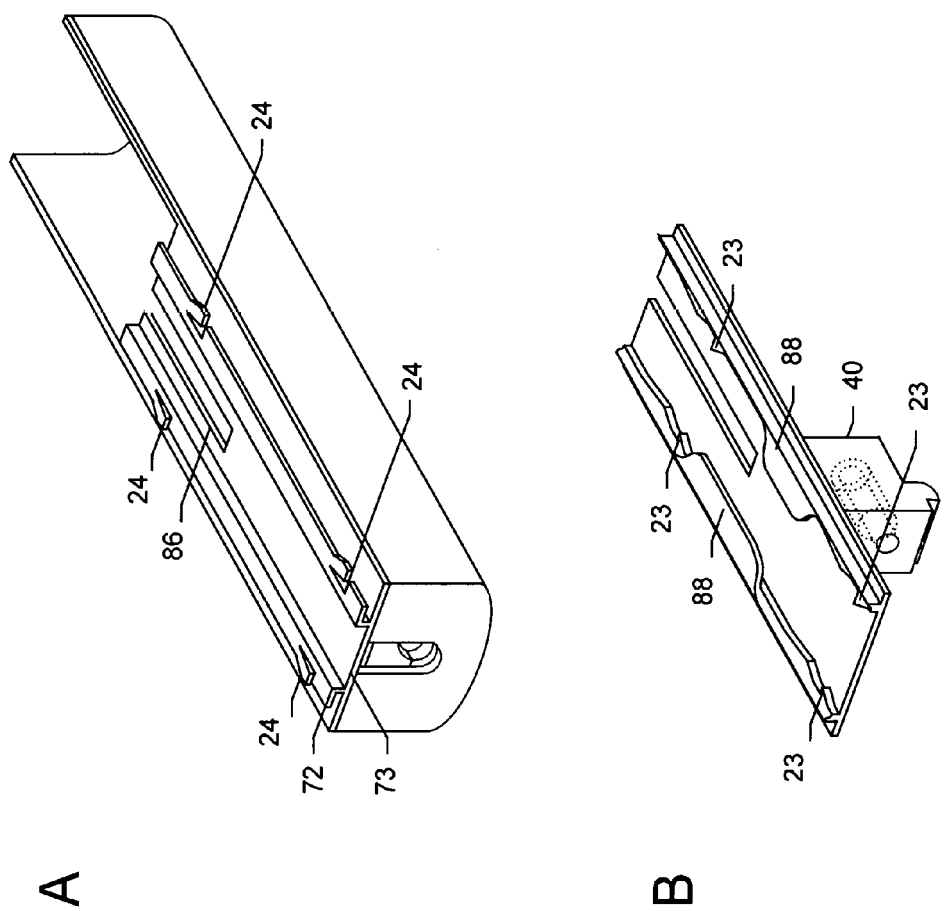
FIG. 6 shows a schematic example of a syringe holder rail lock mechanism.

FIG. 6 shows a schematic example of a syringe holder rail lock mechanism. FIG. 6A shows a view of the bottom plate 73 of the syringe holder that is flipped upside down. An exposed bottom surface of the bottom plate 73 shows a pair of the rails 72 which run longitudinally from a proximal end to a distal end of said bottom plate. Each rail 72 has a pair of rail lock knobs 24. The rail lock knob 24 is configured to be right angled at a proximal end of said knob to the longitudinal axis of the rail 72 and tapered at a distal end of said knob. The rail knob 24 is configured as horizontally and reversibly depressible, having a triangular fissure located medially along the longitudinal axis for a length from the proximal end of said knob. FIG. 6B shows an exposed view of the syringe holder rail locks 23 located under a cut-out view 88 of the syringe holder thrust rails 76. The syringe holder thrust rail lock is configured to be right angled at a distal end of said lock to the longitudinal axis of said thrust rail 76 and tapered at a proximal end of said thrust rail. Distal to the right angled distal end of the rail lock 23, there is provided a longitudinal recess in which a corresponding rail lock knob 24 slides. The configurations of both rail locks 23 and rail lock knobs 24 allow each said rail lock knob to longitudinally move forward only to the right angled end of the corresponding rail lock and to slide out distally without hindrance.

Figure 7:
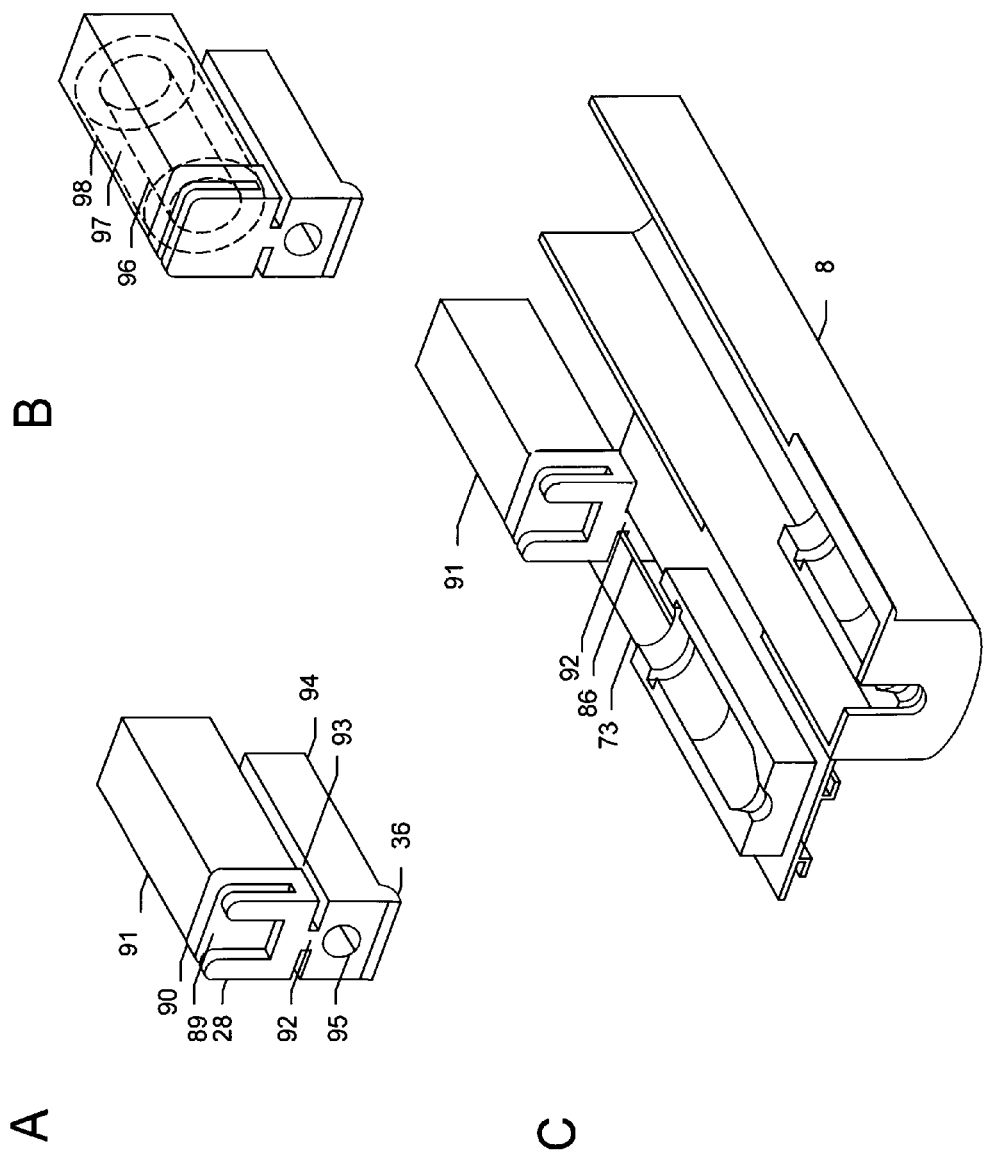
FIG. 7 shows a schematic example of a plunger thrust.

FIG. 7 shows a schematic example of a plunger thrust 28. FIG. 7A depicts individual components of the plunger thrust which is provided as one or a plurality of configurations including a two-part configuration of an upper part 91 connecting to a lower part 94 via a plunger thrust neck 92. The upper part 91 of the plunger thrust sits atop the bottom plate 73 of the syringe holder and the lower part 94 of said plunger thrust is located in the syringe propulsion assembly compartment. The plunger thrust neck 92 slidably is inserted in the syringe holder plunger slot 86 and the syringe holder thrust plunger slot 80 and longitudinally moves inside each said slot 86 and 80. A circular plunger knob of a syringe is reversibly inserted in a plunger groove 89 and is abutted by a plunger thrust collar 90. In a center of the lower part 94 of the plunger thrust, there is provided a central tubular conduit 95 through which the plunger thrust guide shaft 37 passes, as illustrated in FIG. 2A. FIG. 7B shows a view of an inner tubular space 97 of the plunger thrust 28 where a compression spring is inserted in. Said inner tubular space 97 is formed by an inner wall of an outer tubular cylinder 98 and a solid longitudinal cylinder 96 axially protruding from a distal surface of the plunger thrust collar 90 to a center of said space. The compression spring inside the cylindrical tubular space 97 pushes the plunger thrust 28 forward once the ratchet 36 of said plunger thrust 28 is released from the pawl 35, as illustrated in FIG. 2A. FIG. 7C shows an assembled view of the plunger thrust 28 with the open syringe holder. The upper part 91 of the plunger thrust sits atop the bottom plate 73 of the syringe holder 8 and the plunger thrust neck 92 is inserted in the syringe holder plunger slot 86.

Figure 8:
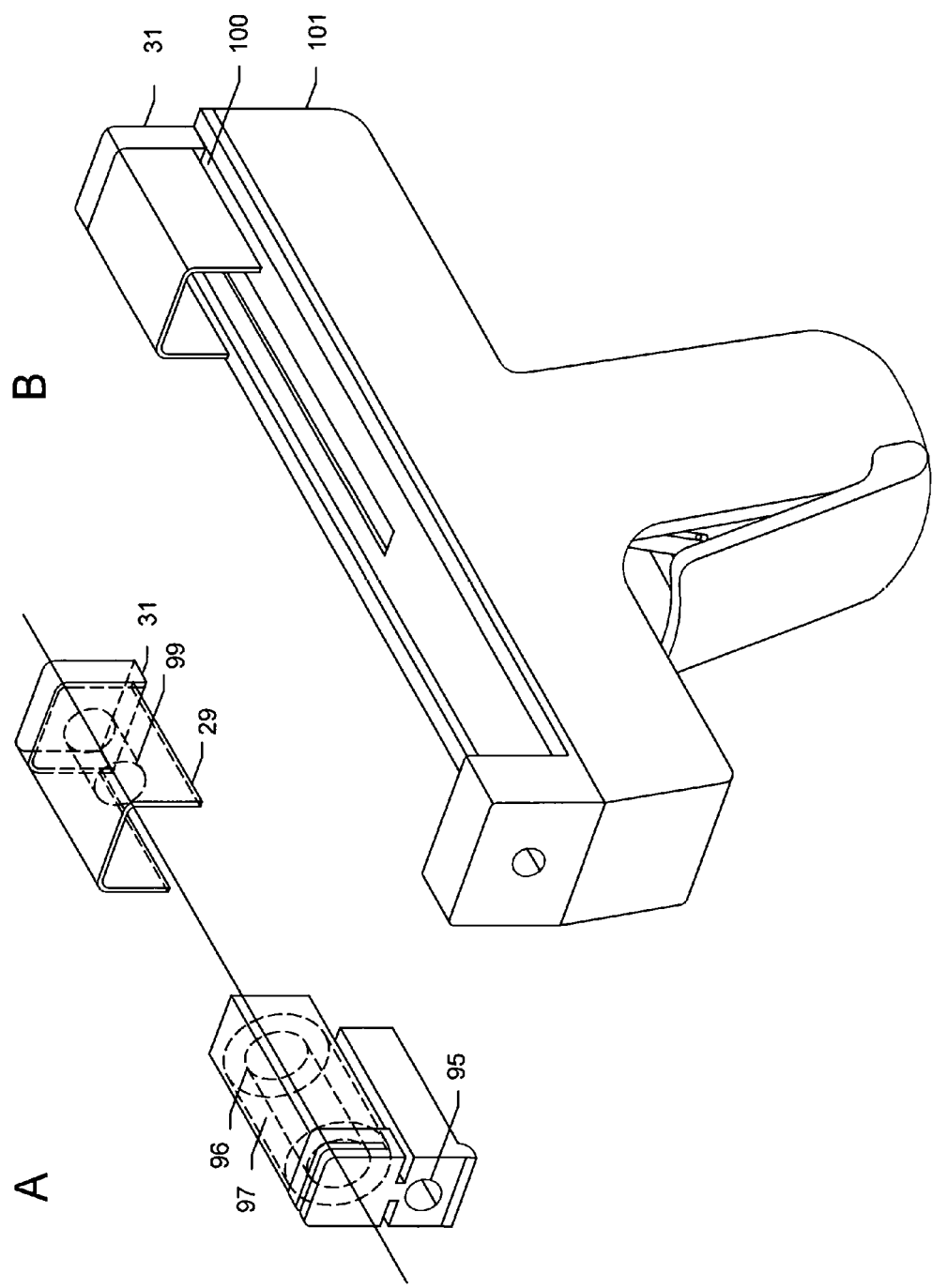
FIG. 8 shows a schematic example of a plunger thrust housing.
Figure 9:
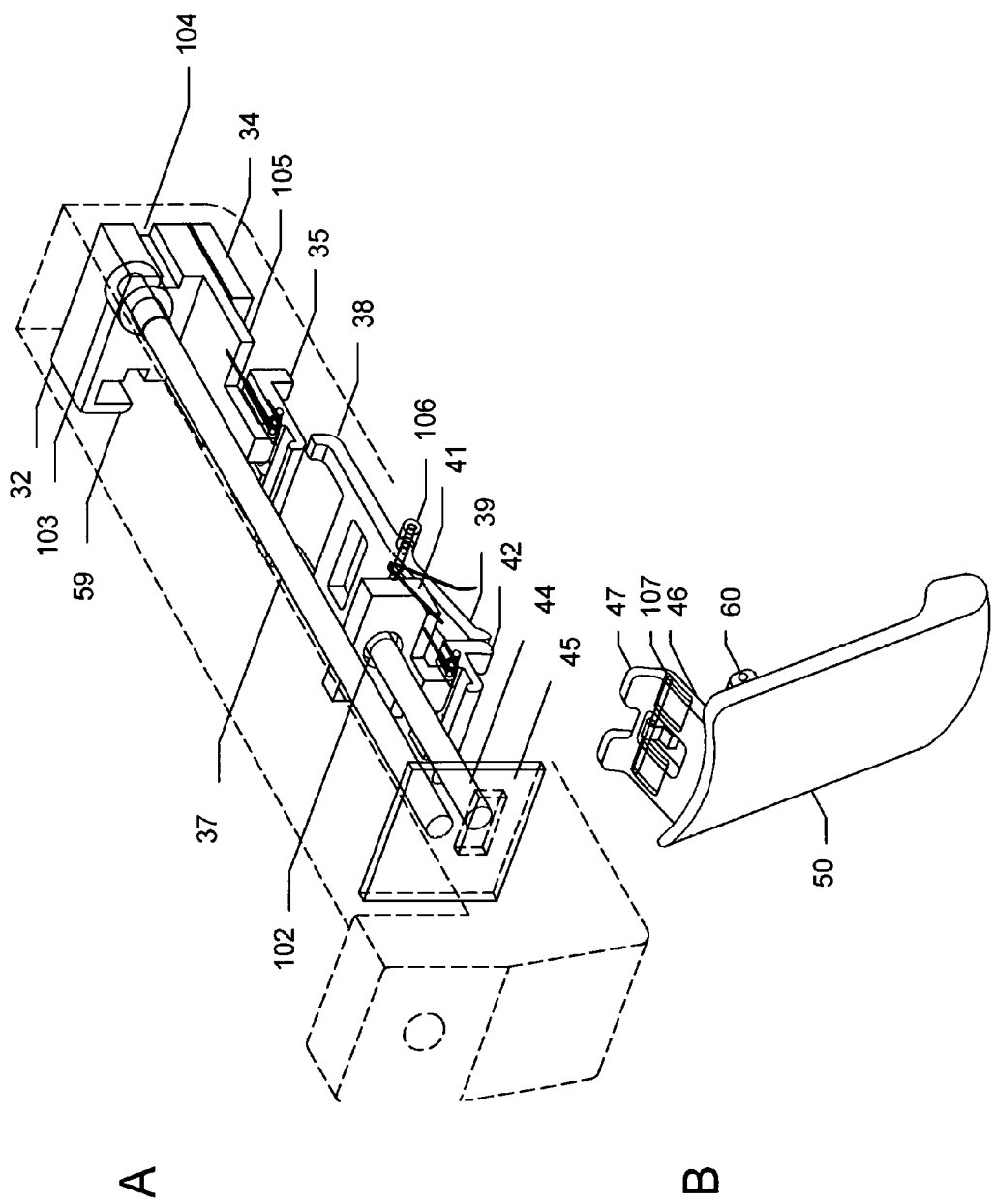
FIG. 9 illustrates a schematic example of a syringe propulsion assembly (FIG. 9A) and a part of a trigger assembly (FIG. 9B).

FIG. 8 shows a schematic example of a plunger thrust housing 29. FIG. 8A shows a schematic illustration of the plunger thrust housing and a method of engagement of the plunger thrust with said plunger thrust housing. The plunger thrust housing is provided as one or a plurality of configurations including a rectangular tubular configuration having a rectangular tube 29 without a bottom wall and a closed rectangular wall 31 at a distal end. A height of the rectangular tube 29 is shorter than a height of the distal rectangular wall 31 to produce a longitudinally linear slot 100 on each lateral side of the plunger thrust housing. The linear slot 100 of the plunger thrust accommodates the bottom plate 73 of the syringe holder 8 for longitudinally distal movement of said syringe holder toward the distal rectangular wall 31. The distal movement of the syringe holder 8 cocks both the syringe holder thrust 40 and plunger thrust 28 for a new round of injection. In a center of an inner surface of the distal rectangular wall 31, there is provided a solid cylinder 99 which slides in the compression spring of the plunger thrust for a length to provide said compression spring with an axial positioning support. FIG. 8B shows a schematic view of the plunger thrust housing assembled with the apparatus. A distal end of the rectangular wall 31 of the plunger thrust housing is fixedly aligned with a distal end 101 of the syringe propulsion assembly compartment.

FIG. 9A shows a schematic example of the syringe propulsion assembly housed in the syringe holder assembly compartment. Referring to FIGS. 2A and 5B, the central tubular conduit 84 of the syringe holder thrust 40 moves longitudinally over the guide shaft 44 from a proximal end of the syringe holder guide shaft assembly 41 toward the proximal panel 45 of the syringe propulsion assembly compartment. Linear propulsion of the syringe holder thrust 40 is accomplished by expansion of a compression spring housed in a cylindrical tubular space 102 of the syringe holder guide shaft assembly 41 and the cylindrical tubular space 83 of said thrust 40. Referring to FIGS. 2A and 7A, the central tubular conduit 95 of the plunger thrust 28 moves longitudinally over the guide shaft 37 from a proximal end of the syringe holder positioner 32 toward said proximal panel 45. Linear propulsion of the plunger thrust 28 is accomplished by expansion of a compression spring housed in a cylindrical tubular space 103 of the syringe holder positioner and in the cylindrical tubular space 97 of said plunger thrust 28. The syringe holder positioner 32 sits atop the syringe holder positioner supporter 34 and is slidably movable along the longitudinal axis, guided by a pair of syringe holder positioner slots 104 on both lateral sides of said positioner which slide over a pair of corresponding rails protruding from an inner wall of the syringe propulsion assembly compartment. The plunger thrust pawl release lever 38-39 pivots about a pair of plunger thrust pawl release lever joints 106 which are attached to the inner wall of the syringe propulsion assembly compartment. FIG. 9B shows a part of the trigger assembly, comprising the trigger lever 50, the trigger bar tip 47 fixedly attached to the trigger lever by the trigger bar 46 and a pair of trigger connecting rod hinge joints 60. The trigger bar 46 is stabilized by a trigger bar guide pin 107 which is horizontally inserted in a longitudinally curvilinear slot in the trigger bar. The trigger bar guide pin 107 is fixed to a center hub which is attached to an inner surface of the outer wall of the handle 54.

Figure 10:
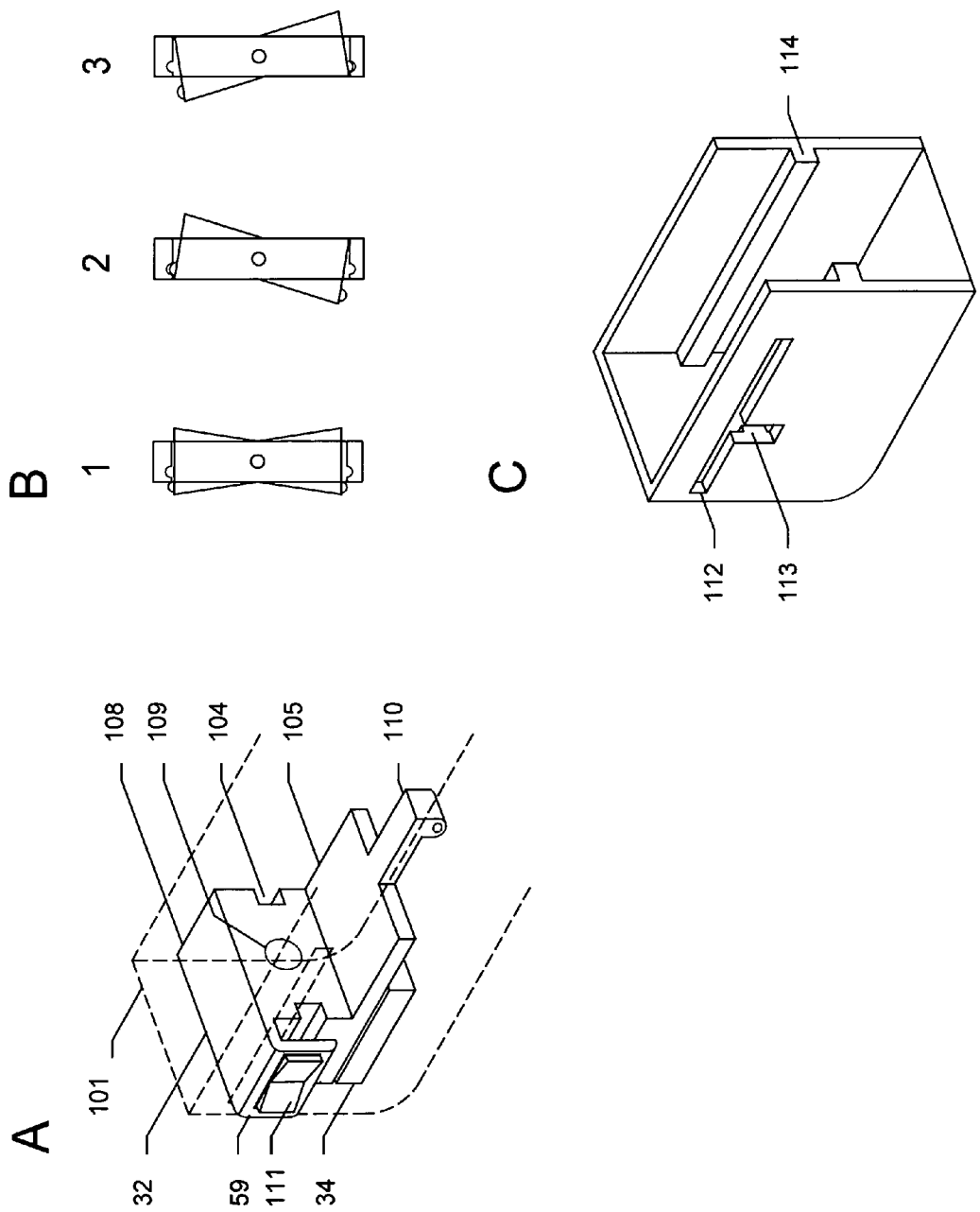
FIG. 10 shows a schematic example of a syringe holder positioner.

FIG. 10 shows a schematic example of the syringe holder positioner. FIG. 10A illustrates a schematic layout of the syringe holder positioner, provided as one or a plurality of configurations including a rectangular box configuration of a main body 108 of said positioner 32. The main body 108 has a pair of longitudinally linear slots 104 located on both lateral sidewalls, a tubular conduit 109 located in a center of said main body for the plunger thrust guide shaft 37, the syringe holder positioner knob 59 fixedly attached to one upper longitudinal border of one lateral side, a syringe holder positioner bottom plate 105 anteriorly protruding from a lower proximal end of said main body and a hinge joint 110 for the plunger thrust pawl protruding from a central part of the bottom plate 105. Referring to FIG. 9A, the cylindrical tubular space 103 for the compression spring is located inside the main body 108 behind the tubular conduit 109. The syringe holder positioner knob 59 comprises a syringe holder positioner release switch 111 which either locks or unlocks the syringe holder positioner, as depicted in FIG. 10B. FIG. 10B shows top-down views of the release switch 111 illustrating mechanisms of locking and unlocking the syringe holder positioner. B1 shows a neutral state of the release switch, B2 shows an inward depression of a distal part of the switch and B3 shows a similar inward depression of a proximal part of the switch. FIG. 10C shows a schematic example of the syringe holder positioner housing adjoining the distal end of the syringe propulsion assembly compartment which houses said syringe holder positioner 32. The syringe holder positioner knob 59 slidably moves in a slot 112 and either the proximal or distal part of the syringe holder positioner release switch gets in a vertical slot 113 to anchor said release switch in a locked or unlocked position. The syringe holder positioner slot 104 slidably moves over a corresponding rail 114 located on each vertical inner wall of the compartment.

Figure 11:
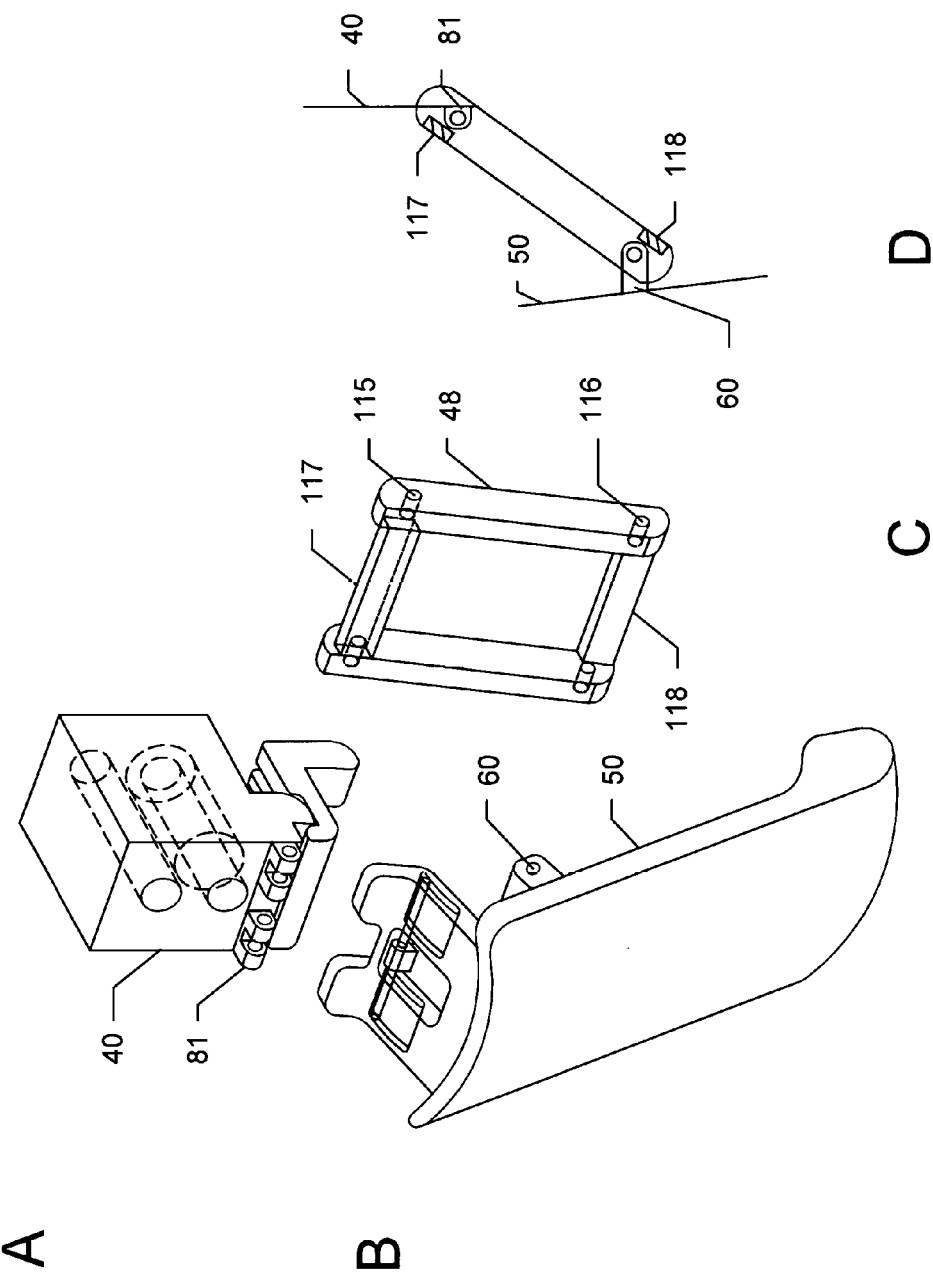
FIG. 11 illustrates a schematic example of a trigger assembly illustrating components of trigger withdrawal mechanism.

FIG. 11 illustrates a schematic example of components of the trigger assembly illustrating a trigger withdrawal mechanism. FIG. 11A depicts the hinge joint 81 fixedly located at the bottom proximal edge of the syringe holder thrust 40 and FIG. 11B shows one of a pair of the trigger connecting rod hinge joints 60 attached to the inner wall of the trigger lever 50 of the trigger assembly. FIG. 11C shows a trigger connecting rod assembly which comprises a pair of the trigger connecting rods 48, and an upper 117 and lower 118 horizontal bars provided as one or a plurality of configurations including a rectangular bar. An upper end of the trigger connecting rod 48 is rotatably connected to the hinge joint 81 via a pivoting pin that is inserted in an upper pivoting tubular conduit 115 and a lower end of said trigger connecting rod is similarly connected to the hinge joint 60 via a pivoting pin that is inserted in an upper pivoting tubular conduit 116. FIG. 11D shows a profile view of the trigger connecting rod assembly. The lower horizontal bar 118 connected to the joint 60 of the trigger lever 50 is located below said joint 60 along the longitudinal axis. The upper horizontal bar 117 connected to the joint 81 of the syringe holder thrust 40 is located above said joint 81. Asymmetric placement of the horizontal bars above and below the hinge joints 60 and 81 along the longitudinal axis of the connecting rods 48 allows unobstructed inward and outward movements of the trigger lever 50 to and from the handle assembly. Upon a release of the trigger lever back to the original and un-squeezed position, the trigger connecting rods 48 push back the syringe holder thrust 40 for a distance by a circumferentially downward pressure on the hinge joint 81 of said syringe holder thrust generated by the horizontal bar 117.

Figure 12:
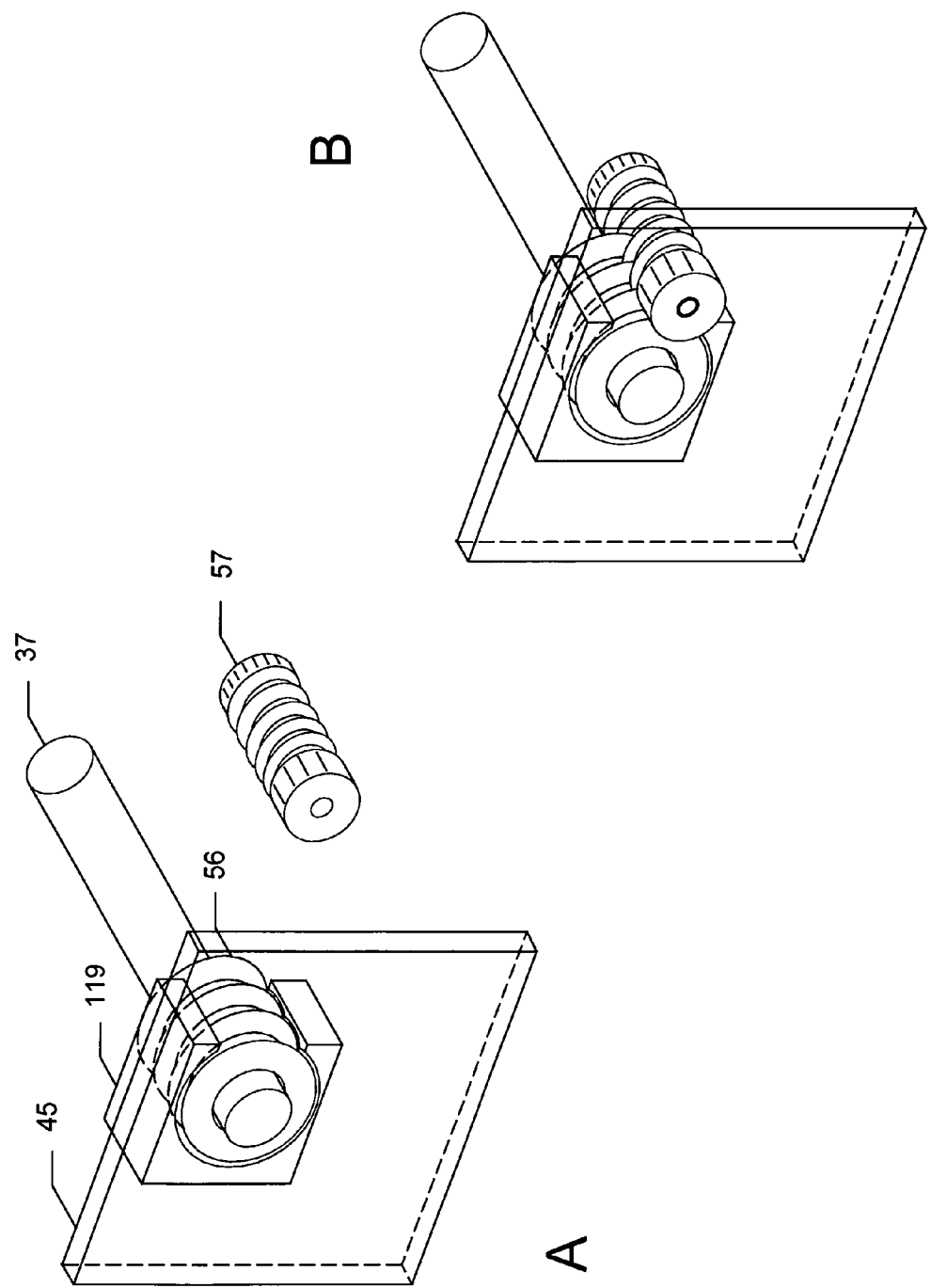
FIG. 12 shows a schematic example of a needle depth control device.

FIG. 12 shows a schematic example of the needle depth control device. FIG. 12A shows the needle depth control device which comprises the proximal panel 45 of the syringe propulsion assembly compartment, an internally threaded nut 119 fixedly attached to the distal surface of said proximal panel 45, the needle depth control thread 56 which is rotatably threaded in said threaded nut 119 and the spiral needle depth control knob 57. The plunger thrust guide shaft 37 is slidably inserted in the needle depth control thread 56. A proximal end of the spiral needle depth control knob 57 is rotatably attached to the distal surface of the proximal panel 45 and said control knob rotates along a longitudinal axis. FIG. 12B shows an assembled view of the needle depth control device. The needle depth control thread 56 is spirally coupled in parallel with the spiral needle depth control knob 57 which is accessible from outside the syringe propulsion assembly compartment. Rotation of the spiral needle depth control knob 57 rotationally moves the needle depth control thread 56 away from or toward the proximal panel 45, dependent on handedness of the spirals.

Figure 13:
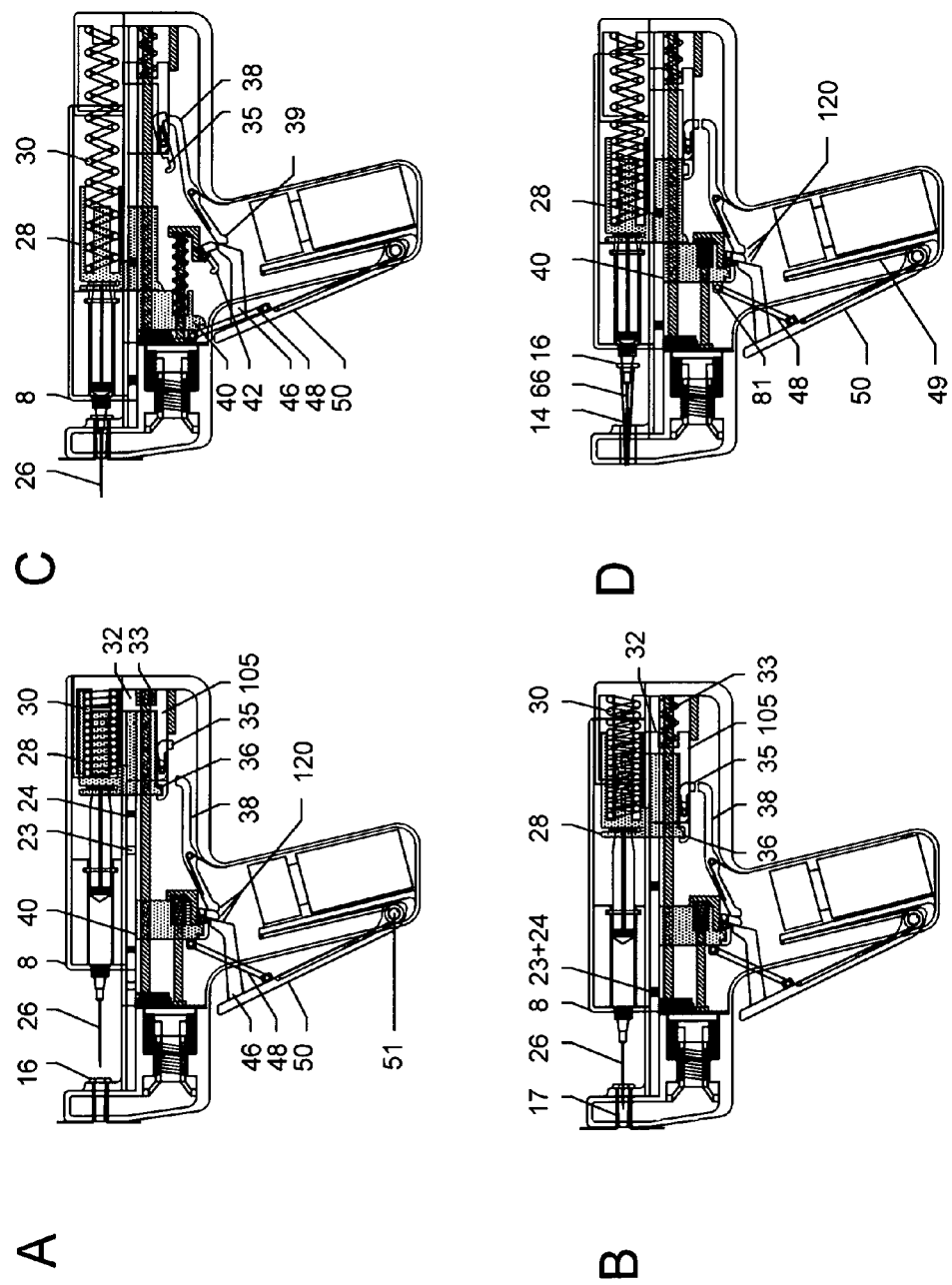
FIG. 13 shows a full mechanical sequence of the apparatus starting from loading a syringe (13A), followed by positioning the needle inside the vibration chamber (13B), by penetration of the needle and injection of an agent into a tissue (13C), by retrieval of the syringe holder by the trigger withdrawal (13D), by re-cocking of both the syringe holder thrust and plunger thrust (13E) and by making ready the apparatus with a new barrier device in place for the next round of injection (13F).
Figure 13:
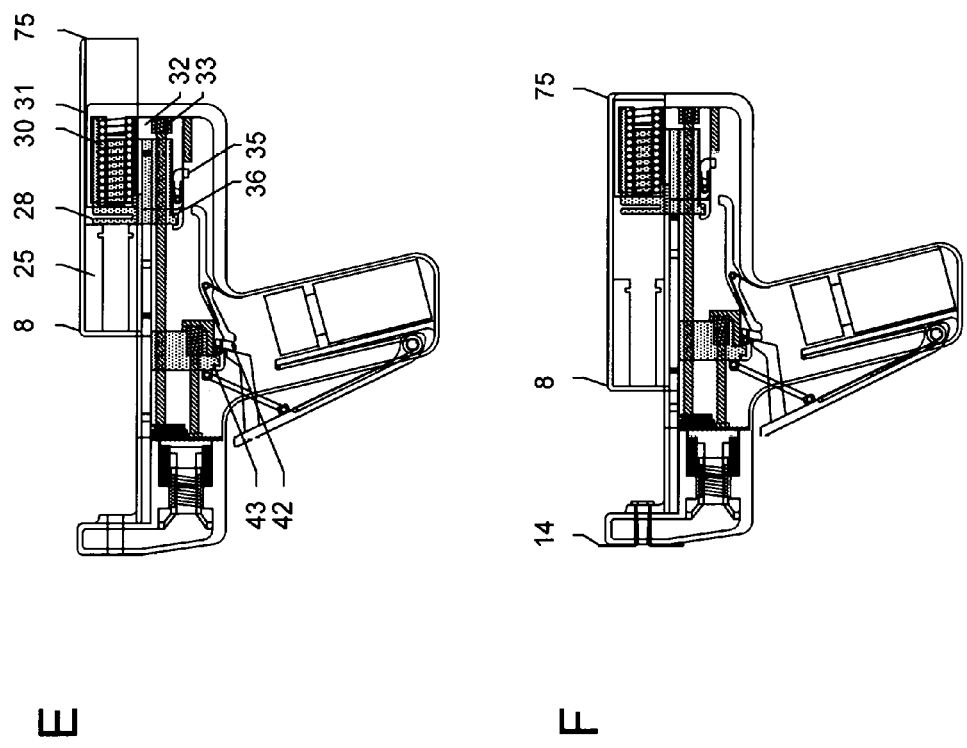

FIG. 13 shows a full mechanical sequence of the apparatus. FIG. 13A depicts a syringe loaded into the syringe cradle 25 of the syringe holder 8 and the needle 26 connected to a syringe hub that protrudes from the syringe holder 8. Both the syringe holder thrust 40 and plunger thrust 28 are drawn back and the syringe positioner 32 is drawn back and retracted to the distal end of the syringe propulsion assembly compartment. The trigger lever 50 is outwardly pushed about the hinge joint 51 of the handle and a trigger mechanism 120 is not activated. The trigger mechanism 120 comprises the trigger bar tip, the distal end of the syringe holder thrust pawl and the proximal knob of the plunger thrust pawl release lever, with all three components arranged in tandem.

FIG. 13B shows a horizontally forward positioning of the syringe holder assembly by forward movement of the syringe holder positioner 32, which engages the needle 26 with the linear tubular conduit 17 of the vibration chamber. It also engages the plunger thrust pawl 35 with the plunger thrust pawl release lever 38. FIG. 13C shows a forward propulsion of both the syringe holder thrust 40 and plunger thrust 28 by squeezing the trigger lever 50 toward the handle, thereby lifting off both the syringe holder thrust pawl 42 and plunger thrust pawl 35. The forward propulsion of the syringe holder thrust and plunger thrust makes the needle 26 penetrate a tissue and inject an agent into said tissue, respectively. FIG. 13D illustrates an withdrawal of the syringe holder by releasing the trigger lever 50. A pair of the trigger connecting rods 48 joined at the syringe holder joint 81 are circumferentially pulled down by an outward rotation of the trigger lever 50 about the hinge joint 51, which translates into a backward push on the syringe holder thrust 40. The barrier ring 16 of the removable and disposable barrier device is adherently attached to the needle hub and is pulled out together with the needle. When pulled through the linear tubular conduit 17 of the vibration chamber, the barrier sheet 14 forms a corrugated tubular encasement around the needle, thereby isolating the needle from the apparatus and preventing contamination of said apparatus. FIG. 13E shows re-cocking of both the syringe holder thrust and plunger thrust by pulling back the syringe holder 8. A distal end of the syringe cradle 28 abuts the proximal end of the plunger thrust 28 and pushes said proximal end of said plunger thrust back until both the plunger thrust pawl 35 and the syringe holder thrust pawl 42 catch the plunger thrust ratchet 36 and the syringe holder thrust ratchet 43, respectively. FIG. 13F shows the apparatus ready for a new round of injection, with the barrier sheet 14 covering the contact portion of the vibration chamber and the syringe holder 8 in a neutral, unengaged position.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A vibration analgesia injection apparatus comprising a vibration assembly
    located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and
    which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:
    the vibration chamber comprising an upper vibration chamber vertically adjoining a lower vibration chamber, which resonates vibration;
    the upper vibration chamber, provided as a mechanical configuration, which has a proximal end, a distal end and a linear tubular conduit centrally located along the longitudinal axis through both ends;
    the proximal end, which contacts a skin overlying the tissue of the recipient through the barrier device and which transmits vibration to the tissue of the recipient; and
    the linear tubular conduit, through which the needle passes from the distal end of said upper vibration chamber to the tissue of the recipient and which accommodates a barrier tube of the barrier device; and the lower vibration chamber, provided as a mechanical configuration, which distally adjoins a vibration panel of the vibration generator, which opens to the upper vibration chamber and which transmits vibration from said vibration panel to said upper chamber.

2. The vibration analgesia injection apparatus according to claim 1, wherein the vibration chamber having a configuration of an airtight resonant space inside said vibration chamber resonates vibration transmitted to said vibration chamber from the vibration generator.

3. The vibration analgesia injection apparatus according to claim 1, wherein the vibration chamber is configured to deliver vibration to the recipient in and around the needle penetration site of the recipient.

4. A method of using the vibration analgesia injection apparatus of claim 1, comprising:
    contacting the skin overlying the tissue of the recipient by the proximal end of the vibration chamber of the vibration assembly through a barrier sheet of the barrier device;
    turning on an electronic switch of the handle assembly to provide the vibration generator with electric power;
    producing vibration from the vibration generator and transmitting said vibration to the vibration panel attached in front of the vibration generator;
    producing resonant vibration inside the vibration chamber; and
    transmitting the resonant vibration to the skin overlying the tissue of the recipient.

5. A vibration analgesia injection apparatus comprising a vibration assembly located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:
    the syringe propulsion assembly comprising a syringe holder thrust assembly attached to a bottom of a syringe holder, a plunger thrust assembly longitudinally aligned with said syringe holder thrust assembly and a syringe holder positioning assembly placed behind said plunger thrust assembly, which is configured to reversibly and forwardly move the syringe holder and a plunger of the syringe along the longitudinal axis;

the syringe holder thrust assembly, which is provided as an operating device having a mechanical configuration, which comprises a pair of syringe holder thrust rails disposed laterally on a syringe holder thrust plate, a syringe holder thrust fixedly attached to an undersurface of the syringe holder thrust plate, a ratchet and pawl device on a bottom surface of the syringe holder thrust and a compression spring disposed in a central longitudinal tubular space of the syringe holder thrust, which reversibly locks and releases the syringe holder thrust by the ratchet and pawl device, which forwardly and reversibly advances said syringe holder thrust by decompression of said compression spring in said syringe holder thrust and which is configured to introduce the needle to the tissue of the recipient through a linear tubular conduit of the vibration chamber;

the plunger thrust assembly, which is provided as an operating device having a mechanical configuration, which comprises an upper part having a plunger thrust located proximally to a compartment enclosing a compression spring and a lower part having a ratchet and pawl device of the plunger thrust assembly disposed on a undersurface of the lower part, which reversibly locks and releases the plunger thrust by the ratchet and pawl device of the plunger thrust assembly, which forwardly and reversibly advances said plunger thrust by decompression of said compression spring enclosed in the said compartment behind said plunger thrust and which is configured to forwardly push the plunger of the syringe to inject an agent to the tissue of the recipient; and the syringe holder positioning assembly, which is provided as an operating device having a mechanical configuration, which comprises a syringe holder positioner and a syringe holder positioner release switch, which is configured to forwardly advance the syringe holder to engage the needle of the syringe housed in said syringe holder with the linear tubular conduit of the vibration chamber and which reversibly locks and unlocks the syringe holder positioner by locking and unlocking the syringe holder positioner release switch, respectively.

6. A method of using the vibration analgesia injection apparatus of claim 5, comprising:

aligning the pawl of the syringe holder thrust in contact with a proximal knob of a pawl release lever of the plunger thrust in tandem distally to a trigger bar tip along the longitudinal axis of the syringe movement assembly;

forwardly positioning the syringe holder assembly that holds the syringe attached to the needle to engage the pawl of the plunger thrust with a distal knob of the pawl release lever by forwardly sliding the syringe holder along the longitudinal axis of the syringe movement assembly;

squeezing the trigger lever toward the handle assembly;

pushing the trigger bar tip distally to simultaneously release the pawl of the syringe holder thrust and rotatably push down the proximal knob of the pawl release lever of the plunger thrust;

releasing the pawl of the plunger thrust by upward pivoting of the distal knob of the pawl release lever; and penetrating the tissue of the recipient with the needle of the syringe and injecting the agent into the tissue of the recipient simultaneously.

7. A method of using the vibration analgesia injection apparatus of claim 5, comprising:

aligning the pawl of the syringe holder thrust separated by a distance from a proximal knob of a pawl release lever of the plunger thrust in tandem distally to a trigger bar tip along the longitudinal axis of the syringe movement assembly;

forwardly positioning the syringe holder assembly that holds the syringe attached to the needle to engage the pawl of the plunger thrust with a distal knob of the pawl release lever by forwardly sliding the syringe holder along the longitudinal axis of the syringe movement assembly;

squeezing a trigger lever toward the handle assembly;

pushing the trigger bar tip half-way distally to release the pawl of the syringe holder thrust and advancing the syringe holder thrust;

penetrating the tissue of the recipient with the needle of the syringe;

pushing the trigger bar tip to a full extent to rotatably push down the proximal knob of the pawl release lever of the plunger thrust about the plunger thrust pawl release lever joint;

releasing the pawl of the plunger thrust by upward pivoting of the distal knob of the pawl release lever; and injecting the agent into the tissue of the recipient.

8. A method of using the vibration analgesia injection apparatus of claim 5, comprising:

aligning the pawl of the syringe holder thrust and a proximal knob of a pawl release lever of the plunger thrust in tandem distally to a trigger bar tip along the longitudinal axis of the syringe movement assembly;

forwardly positioning the syringe holder assembly that holds the syringe attached to the needle to engage the pawl of the plunger thrust with a distal knob of the pawl release lever by forwardly sliding the syringe holder along the longitudinal axis of the syringe movement assembly;

squeezing the trigger lever toward the handle assembly;

pushing the trigger bar tip to release the pawl of the syringe holder thrust and rotatably push down the proximal knob of the pawl release lever of the plunger thrust;

releasing the pawl of the plunger thrust by upward pivoting of the distal knob of the pawl release lever;

penetrating the tissue of the recipient with the needle of the syringe and injecting the agent into the tissue of the recipient.

9. A vibration analgesia injection apparatus comprising a vibration assembly located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:

the syringe holder assembly comprising a syringe holder and a syringe holder rail assembly connected to a bottom of said syringe holder, which is provided as an operating device having a mechanical configuration, which is configured to releasably enclose the syringe and the needle, which is axially aligned with an upper vibration chamber and which inserts said needle in a linear tubular conduit of said vibration chamber;

the syringe holder comprises an opening at a proximal end through which a syringe hub protrudes, an open distal end and a syringe cradle, which is configured to securely house the syringe and which is configured to reload the syringe propulsion assembly; and the syringe holder rail assembly comprises a plurality of rails and reversible rail locks, which is configured to slidably move the syringe holder along the longitudinal axis and which is configured to reversibly lock the syringe holder in a forward direction.

10. The vibration analgesia injection apparatus according to claim 9, wherein the barrier device is configured to be inserted in a linear tubular conduit of the vibration chamber from the proximal to the distal end of said vibration chamber and to be pulled out in the same proximal-to-distal direction by a retracting needle hub securely attached to a ring of said barrier device.

11. A vibration analgesia injection apparatus comprising a vibration assembly located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:

the handle assembly comprising an outer wall of a handle, a pair of hinge joints located at a proximal end of a bottom of said handle assembly on both sides, an inner handle divider, a battery pack and a control electronics and an electronic switch located on a side of said handle assembly;

the outer wall of the handle, which is attached to a bottom of a syringe propulsion assembly compartment and which comprises a plurality of openings on an anterior part of said outer wall to accommodate a trigger assembly;

the hinge joints, which provides a trigger lever with a pivotal attachment and which is encircled by a trigger torsion spring for each said hinge joint;

the inner handle divider, which is provided as a separating wall inside the handle and which is configured to provide an anterior space for the trigger torsion springs and a posterior space for the battery pack and the control electronics;

the battery pack and the control electronics, which is electrically connected to the vibration generator and which provides said vibration generator with power and electronic control for frequency and amplitude of vibration; and the electronic switch, which is electrically connected to both the vibration generator and the battery pack/control electronics, which turns on and off the vibration generator, which varies frequencies and amplitudes of vibration by a plurality of pre-set numbers of push-to-make and push-to-break actions on said switch.

12. A method of using the vibration analgesia injection apparatus of claim 7, comprising:

aligning a pawl of a syringe holder thrust and a proximal knob of a pawl release lever of a plunger thrust in tandem distally to a trigger bar tip along the longitudinal axis of the syringe movement assembly;

forwardly positioning the syringe holder assembly that holds the syringe attached to the needle to engage a pawl of the plunger thrust with a distal knob of the pawl release lever by forwardly sliding the syringe holder along the longitudinal axis of the syringe movement assembly;

squeezing the trigger lever toward the handle assembly;

pushing the trigger bar tip distally to release the pawl of the syringe holder thrust and rotatably push down the proximal knob of the pawl release lever of the plunger thrust;

releasing the pawl of the plunger thrust by upward pivoting of the distal knob of the pawl release lever;

penetrating the tissue of the recipient with the needle of the syringe and injecting the agent into the tissue of the recipient simultaneously;

releasing the trigger lever from the handle assembly; and pushing distally the syringe holder thrust by an upper horizontal bar attached to a trigger connecting rods until the syringe holder thrust is fully retracted and locked in by a ratchet and pawl device of the syringe holder thrust.

13. A vibration analgesia injection apparatus comprising a vibration assembly located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:
  the barrier device comprising a sheet at a proximal end, a ring at a distal end, and a barrier tube connecting both the sheet and the ring, which is configured to be releasably inserted in a linear tubular conduit of the vibration chamber and which isolates the vibration chamber from the recipient and from the needle;
  the sheet, which is made of one or a plurality of thin polymer membranes, which merges with a proximal end of the barrier tube at a center of said sheet, which covers the recipient contact side of the vibration chamber and which is configured to form a corrugated tube to encase the needle during withdrawal of said needle;
  the ring, which is made of one or a plurality of elastic polymers, which is connected to a distal end of the barrier tube, which is releasably fastened to an outer wall of a distal end of an upper vibration chamber and which is configured to securely adhere to an outer wall of a needle hub; and
  the barrier tube, which is slidably inserted in the linear tubular conduit of the vibration chamber and which coaxially accommodates the needle.

14. A method of using the vibration analgesia injection apparatus of claim 8, comprising:
  slidably inserting the ring and the barrier tube of the barrier device in the linear tubular conduit of the vibration chamber in the proximal-to-distal direction and releasably fastening the ring to the outer wall of the distal end of the upper vibration chamber;
  unfolding the sheet connected to the proximal end of the barrier tube to cover the recipient contact side of the proximal end of the upper vibration chamber;
  inserting the needle of the syringe in the linear tubular conduit in a distal-to-proximal direction;
  coaxially housing the needle of the syringe placed inside the barrier tube and securely adhering the needle hub to the ring of the barrier device once the needle is placed inside the barrier device;
  pulling the needle with the needle hub securely attached to the ring of the barrier device out from the linear tubular conduit in the proximal-to-distal direction after completion of injection of the agent to the tissue of the recipient; and
  pulling the sheet of the barrier device through the linear tubular conduit in the proximal-to-distal direction and circumferentially encasing the needle by the sheet in a corrugated configuration.

15. A vibration analgesia injection apparatus comprising a vibration assembly located at a proximal end, connected to a syringe movement assembly along a longitudinal axis, a handle assembly connected to a bottom of the syringe movement assembly at an angle and a barrier device removably insertable in the vibration assembly, which is hand-held by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device, which is removably insertable in the vibration chamber and disposable, which covers a recipient contact side of the vibration chamber and which isolates the vibration chamber from the recipient and from the needle:
  the trigger assembly comprising a trigger lever rotatably attached to a pair of hinge joints of the handle assembly, a trigger bar attached to an inner wall of said trigger lever, a trigger bar tip attached to a distal end of said trigger bar, a pair of trigger torsion springs rotatably inserted in the pair of the hinge joints of the handle assembly, a trigger connecting rod assembly comprising a pair of vertical trigger connecting rods and a pair of horizontal bars attached to said vertical trigger connecting rods in a rectangular configuration;
  the trigger lever, which is provided as a mechanical configuration, which rotates about said pair of hinge joints of said handle assembly, which provides said trigger bar with circumferential movement about said pair of hinge joints of said handle assembly and which provides each said vertical trigger connecting rod with a pair of hinge joints about which said vertical trigger connecting rod pivots;
  the trigger bar tip attached to the distal end of the trigger bar, which is provided as a mechanical configuration, which is configured to release both a syringe holder thrust and a plunger thrust by releasing a pawl of the ratchet and pawl device of both the syringe holder thrust and plunger thrust;
  the vertical trigger connecting rods, having a lower end of said trigger connecting rod connected to the pair of the hinge joints of the trigger lever and an upper end connected to a pair of hinge joints of the syringe holder thrust, which is provided as a mechanical configuration, which pivot about both the pair of the hinge joints of the trigger lever and of the syringe holder thrust upon a squeeze and release movement of the trigger lever;
  the horizontal bars, which is provided as a mechanical configuration, comprising an upper horizontal bar and a lower horizontal bar, which is attached at a right angle to each longitudinally opposite end of said vertical trigger connecting rod in a diagonally opposite off-centered configuration along a longitudinal axis of said vertical trigger connecting rods; and
  the upper horizontal bar, which is located in front of the pair of the hinge joints of the syringe holder thrust and which rotatably pushes distally said pair of hinge joints of said syringe holder thrust upon a release of the trigger lever from the handler assembly by recoiling of the trigger torsion springs.

16. A method of controlling a needle depth of a vibration analgesia injection apparatus comprising:
  providing the vibration analgesia injection apparatus having a vibration assembly located at a proximal end, connected to a syringe movement assembly along a longitudinal axis, a handle assembly connected to a bottom of the syringe movement assembly at an angle and a barrier device removably insertable in the vibration assembly, which is handheld by an operator; the vibration assembly, having a vibration generator and a vibration chamber connected to said vibration generator, which generates and delivers vibration to a tissue of a recipient by contact with said tissue and which encircles a needle penetration site of the tissue by said vibration; the syringe movement assembly, having a syringe holder assembly, a syringe propulsion assembly and a trigger assembly, which reversibly inserts a needle of a syringe in and retracts said needle from the tissue of the recipient through said vibration chamber and which delivers an injectable agent to said tissue; the handle assembly, which provides the syringe movement assembly with a mechanical support and which provides the vibration generator with power and electronic control; the barrier device further includes a sheet at a proximal end, a ring at a distal end, and a barrier tube connecting both the sheet and the ring, which is configured to be releasably inserted in a linear tubular conduit of the vibration chamber and which isolates the vibration chamber from the recipient and from the needle; the sheet is configured to covers the recipient contact side of the vibration chamber and form a corrugated tube to encase the needle during withdrawal of said needle; the ring, which is connected to a distal end of the barrier tube, which is releasably fastened to an outer wall of a distal end of an upper vibration chamber and which is configured to securely adhere to an outer wall of a needle hub;

manually rotating a rotatable spiral knob for needle penetration depth control disposed in between a distal surface of a proximal panel of the syringe propulsion assembly and a proximal end of the syringe holder thrust away from said proximal panel of said syringe propulsion assembly to decrease a penetration depth of the needle; and manually rotating the rotatable spiral knob for needle penetration depth control disposed in between the distal surface of the proximal panel of the syringe propulsion assembly and the proximal end of the syringe holder thrust toward said proximal panel of said syringe propulsion assembly to increase the penetration depth of the needle.

* * * * *